(12) United States Patent
Fukuhara

(10) Patent No.: US 7,676,078 B2
(45) Date of Patent: Mar. 9, 2010

(54) INSPECTION METHOD, PROCESSOR AND METHOD FOR MANUFACTURING A SEMICONDUCTOR DEVICE

(75) Inventor: Kazuya Fukuhara, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 1312 days.

(21) Appl. No.: 10/776,591

(22) Filed: Feb. 12, 2004

(65) Prior Publication Data

US 2005/0031974 A1 Feb. 10, 2005

(30) Foreign Application Priority Data

Feb. 13, 2003 (JP) ............................ P2003-035383

(51) Int. Cl.
*G06K 9/00* (2006.01)
*G01B 11/00* (2006.01)
*H01L 21/00* (2006.01)
*G03C 5/00* (2006.01)

(52) U.S. Cl. ................. 382/147; 382/152; 382/149; 382/144; 382/145; 430/311; 430/30; 356/399

(58) Field of Classification Search ......... 382/141–152; 430/30, 311, 5; 355/67, 53; 716/19
See application file for complete search history.

(56) References Cited

U.S. PATENT DOCUMENTS

| 4,718,767 | A | | 1/1988 | Hazama |
| 5,348,837 | A | * | 9/1994 | Fukuda et al. ............. 430/269 |
| 5,666,206 | A | | 9/1997 | Uchiyama |
| 5,703,675 | A | * | 12/1997 | Hirukawa et al. ........... 355/53 |
| 5,710,620 | A | * | 1/1998 | Taniguchi ................... 355/53 |
| 5,777,729 | A | * | 7/1998 | Aiyer et al. ............... 356/237.1 |

(Continued)

FOREIGN PATENT DOCUMENTS

| JP | 5-224396 | 9/1993 |
| JP | 8-272078 | 10/1996 |
| JP | 2928277 | 5/1999 |
| JP | 2000-21732 | 1/2000 |
| JP | 2001-230180 | 8/2001 |
| JP | 2002139406 | 5/2002 |

OTHER PUBLICATIONS

Dunning G. and Lind R. C.; "Demonstration of Image Transmission through Fibers by Optical Phase Conjugation" May 24, 1982 Hughes Research Laboratories, Optical Society of America 1982, vol. 7, No. 11, pp. 558-560.*

(Continued)

*Primary Examiner*—Bhavesh M Mehta
*Assistant Examiner*—Mia M Thomas
(74) *Attorney, Agent, or Firm*—Finnegan, Henderson, Farabow, Garrett & Dunner, L.L.P.

(57) ABSTRACT

An inspection method for an illumination optical system of an exposure tool includes coating a surface of an exposure target substrate with a resist film; placing a plurality of imaging components deviating from an optical conjugate plane of a surface of the resist film; generating a plurality of inspection patterns of the resist film having a plurality of openings, by projecting exposure beams output from a plurality of effective light sources onto the resist film via the imaging components; measuring one of the inspection patterns as a reference image, and processing the reference image so as to provide reference image data; and determining an abnormal inspection image by measuring inspection images of the inspection patterns and comparing a plurality of inspection image data provided by processing the inspection images with the reference image data.

20 Claims, 18 Drawing Sheets

U.S. PATENT DOCUMENTS

| | | | | |
|---|---|---|---|---|
| 5,812,261 A * | 9/1998 | Nelson et al. | ............... | 356/318 |
| 5,815,594 A * | 9/1998 | Tanaka | ............... | 382/151 |
| 5,838,433 A * | 11/1998 | Hagiwara | ............... | 356/364 |
| 5,973,771 A | 10/1999 | Hibbs et al. | | |
| 6,008,880 A * | 12/1999 | Higashiki et al. | ............... | 355/53 |
| 6,014,455 A * | 1/2000 | Sumiyoshi et al. | ............... | 382/144 |
| 6,016,187 A * | 1/2000 | Noguchi et al. | ............... | 355/53 |
| 6,064,484 A * | 5/2000 | Kobayashi et al. | ............... | 356/390 |
| 6,078,738 A * | 6/2000 | Garza et al. | ............... | 716/21 |
| 6,081,330 A * | 6/2000 | Nelson et al. | ............... | 356/318 |
| 6,081,659 A * | 6/2000 | Garza et al. | ............... | 716/21 |
| 6,091,845 A * | 7/2000 | Pierrat et al. | ............... | 382/144 |
| 6,130,747 A * | 10/2000 | Nomura et al. | ............... | 356/239.2 |
| 6,148,097 A * | 11/2000 | Nakayama et al. | ............... | 382/141 |
| 6,172,365 B1 * | 1/2001 | Hiroi et al. | ............... | 250/310 |
| 6,222,195 B1 * | 4/2001 | Yamada et al. | ............... | 250/492.2 |
| 6,272,236 B1 * | 8/2001 | Pierrat et al. | ............... | 382/144 |
| 6,317,198 B1 * | 11/2001 | Sato et al. | ............... | 355/77 |
| 6,327,025 B1 * | 12/2001 | Imai | ............... | 355/53 |
| 6,348,967 B1 * | 2/2002 | Nelson et al. | ............... | 356/432 |
| 6,351,554 B1 * | 2/2002 | Nakayama et al. | ............... | 382/141 |
| 6,373,054 B2 * | 4/2002 | Hiroi et al. | ............... | 250/310 |
| 6,374,397 B1 * | 4/2002 | Miyamoto et al. | ............... | 716/21 |
| 6,396,945 B1 * | 5/2002 | Ishii | ............... | 382/149 |
| 6,445,453 B1 * | 9/2002 | Hill | ............... | 356/450 |
| 6,597,448 B1 * | 7/2003 | Nishiyama et al. | ............... | 356/237.4 |
| 6,700,950 B1 * | 3/2004 | Pellegrini et al. | ............... | 378/34 |
| 6,760,101 B2 * | 7/2004 | Sato et al. | ............... | 356/237.4 |
| 6,842,225 B1 * | 1/2005 | Irie | ............... | 355/67 |
| 6,849,363 B2 * | 2/2005 | Ohashi et al. | ............... | 430/5 |
| 6,853,926 B2 * | 2/2005 | Alfano et al. | ............... | 702/40 |
| 6,884,552 B2 * | 4/2005 | Mieher et al. | ............... | 430/5 |
| 6,921,920 B2 * | 7/2005 | Kazakevich | ............... | 257/81 |
| 6,950,547 B2 * | 9/2005 | Floeder et al. | ............... | 382/143 |
| 6,972,836 B2 * | 12/2005 | Sato et al. | ............... | 356/121 |
| 6,974,653 B2 * | 12/2005 | Leung et al. | ............... | 430/30 |
| 6,982,786 B2 * | 1/2006 | Shiode | ............... | 356/121 |
| 7,061,603 B2 * | 6/2006 | Sato et al. | ............... | 356/237.4 |
| 7,072,040 B2 * | 7/2006 | Fukuhara | ............... | 356/364 |
| 7,101,752 B2 * | 9/2006 | Park et al. | ............... | 438/239 |
| 7,133,550 B2 * | 11/2006 | Hiroi et al. | ............... | 382/145 |
| 7,186,485 B2 * | 3/2007 | Fukuhara et al. | ............... | 430/30 |
| 7,206,442 B1 * | 4/2007 | Herod et al. | ............... | 382/141 |
| 7,221,788 B2 * | 5/2007 | Schulze et al. | ............... | 382/144 |
| 7,231,079 B2 * | 6/2007 | Okuda et al. | ............... | 382/145 |
| 7,266,235 B2 * | 9/2007 | Hiroi et al. | ............... | 382/145 |
| 7,286,216 B2 * | 10/2007 | Fukuhara et al. | ............... | 356/237.1 |
| 7,556,899 B2 * | 7/2009 | Ikeda et al. | ............... | 430/22 |
| 2001/0019407 A1 * | 9/2001 | Sato et al. | ............... | 356/237.4 |
| 2001/0019625 A1 * | 9/2001 | Kenan et al. | ............... | 382/144 |
| 2002/0001759 A1 * | 1/2002 | Ohashi et al. | ............... | 430/5 |
| 2003/0042493 A1 * | 3/2003 | Kazakevich | ............... | 257/98 |
| 2004/0081917 A1 * | 4/2004 | Tanaka et al. | ............... | 430/311 |
| 2004/0207836 A1 * | 10/2004 | Chhibber et al. | ............... | 356/237.4 |
| 2005/0037272 A1 * | 2/2005 | Tanaka | ............... | 430/30 |
| 2005/0250022 A1 * | 11/2005 | Kotani et al. | ............... | 430/5 |

OTHER PUBLICATIONS

Soffer et al.; "Associative Holographic Memory With Feedback Using Phase-Conjugate Mirrors" Sep. 30, 1985 Hughes Research Laboratories, Optical Society of America 1982, vol. 11, No. 2, pp. 118-120.*

Krautschik et al., "Mathematical Treatment of Condenser Aberrations and Their Impact on Linewidth Control", SPIE (Mar. 1999), 3679:87-98.

Notification of Reasons for Refusal Issued by the Japanese Patent Office, mailed Dec. 6, 2005, for Japanese Patent Application No. P2003-035383, and English-language translation thereof.

Search Report, dated Jul. 27, 2007, from the Netherlands Patent Office, in counterpart Netherlands Application No. 135388.

* cited by examiner

INSPECTION METHOD, PROCESSOR AND METHOD FOR MANUFACTURING A SEMICONDUCTOR DEVICE

CROSS REFERENCE TO RELATED APPLICATIONS

This application is based upon and claims the benefit of priority from prior Japanese Patent Application P2003-035383 filed on Feb. 13, 2003; the entire contents of which are incorporated by reference herein.

BACKGROUND OF THE INVENTION

1. Field of the Invention

The present invention relates to photolithography, more specifically, to an inspection method for an illumination optical system of an exposure tool.

2. Description of the Related Art

Accompanying progress of semiconductor manufacturing technology, more specifically, miniaturization of a semiconductor device and enhancement of integration density, the performance specification required for an exposure tool, which transfers a fine pattern onto a semiconductor substrate, has critical. Since a variation in dimensions of a pattern which configures a semiconductor device, affects the operating speed of the semiconductor device, an exposure process is required to transfer a uniform resist pattern with high precision in a one-shot exposure region.

In the exposure process of photolithography, a photomask on which a mask pattern including a transparent portion, an opaque portion, and a translucent portion is delineated, is uniformly illuminated by illumination beams from an illumination optical system so as to project a mask pattern image onto a one-shot exposure region on a semiconductor substrate using a projection optical system. Since a resist film is coated on the surface of the semiconductor substrate, a resist pattern is formed on the semiconductor substrate by a development process after exposure.

The illumination optical system of the exposure tool includes a fly's eye lens and a condenser lens. The fly's eye lens receives illumination beams from a light source, and forms effective light sources on an output side of the fly's eye lens. The condenser lens gathers the emerged beams from the output side of the fly's eye lens, and uniformly illuminates a region on which the mask pattern of the photomask is delineated.

Due to various characteristics of the illumination optical system of the exposure tool, pattern dimensions that need to be of the same dimension may vary in the one-shot exposure region. A reason for a variation in the pattern dimensions, for example, may be uneven illumination, where intensity of the illumination beams illuminating the photomask (hereinafter, referred to as an "exposure dose"), varies from place to place. When a pattern dimension almost substantially equal to or less than the wavelength of the illumination beam, an exposure with an exposure dose different from an optimum exposure dose causes a variation of a transferred resist pattern dimension. Since the finer the pattern dimension, the smaller the allowable exposure dose range (exposure latitude) for formation of a resist pattern with a desired dimension, the uneven illumination must be strictly controlled. The uneven illumination is caused by a local defect, such as dust or a scratch on a surface of a lens included in the illumination optical system.

Another factor that causes a variation in resist pattern dimensions in a one-shot exposure region is a variation in the shape of an effective light source, in particular, a variation in a size thereof ($\sigma$ value). Since the $\sigma$ value is one of the factors that determine an imaging characteristic of a lens, the variation in the $\sigma$ value represents changes in resolution and exposure latitude. In addition, in recent years, a modified illumination such as annular illumination is actively utilized for improving resolution. In this case, in addition to the $\sigma$ value, the variation of an annular shield factor in the one-shot exposure region causes a variation of the resist pattern dimension. For example, the $\sigma$ value varies due to an aberration of the condenser lens located between the effective light source and the photomask, and the variation of the resist pattern dimension occurs (Proceedings of SPIE, March, 1999, Vol. 3679, p. 87-98).

An inspection method for an exposure tool has been disclosed, in which an illumination distribution is measured on an aperture stop of the projection optical system or on a conjugate position of the aperture stop (Japanese Patent Laid Open No. 2928277).

The variation of the resist pattern dimension in the one-shot exposure region may result from various factors such as not only a local defect of the illumination optical system, but also an aberration and flare of the projection optical system, a dimensional error of the mask pattern on the photomask, a variation of a coated thickness of the resist film, nonuniformity of development, or the like. Accordingly, whether or not the illumination optical system of the exposure tool causes the variation of the resist pattern dimension may not be determined only by inspecting the transferred resist pattern for manufacturing a semiconductor device.

In the method disclosed in Japanese Patent Laid Open No. 2928277, it is necessary to install an illumination distribution detection unit in an appropriate position in the exposure tool. Thus, the configuration of the exposure tool maybe more complex. In addition, an exposure tool which does not have an illumination distribution detection unit cannot perform inspection.

SUMMARY OF THE INVENTION

A first aspect of the present invention inheres in an inspection method for an illumination optical system of an exposure tool including coating a surface of an exposure target substrate with a resist film; placing a plurality of imaging components deviating from an optical conjugate plane of a surface of the resist film; generating a plurality of inspection patterns of the resist film having a plurality of openings, by projecting exposure beams output from a plurality of effective light sources onto the resist film via the imaging components; measuring one of the inspection patterns as a reference image, and processing the reference image so as to provide reference image data; and determining an abnormal inspection image by measuring inspection images of the inspection patterns and comparing a plurality of inspection image data provided by processing the inspection images with the reference image data.

A second aspect of the present invention inheres in a processor for inspecting an illumination optical system of an exposure tool including a data input module configured to acquire a reference image and inspection images of a plurality of inspection patterns of a resist film having a plurality of openings, the inspection patterns obtained by projecting exposure beams output from a plurality of effective light sources onto the resist film coated on a surface of an exposure target substrate by a plurality of imaging components, the imaging components placed so as to deviate from an optical conjugate plane of the surface of the resist film; an image processing module configured to calculate reference image data and inspection image data from the reference image and the inspection images, respectively; and a determination module configured to compare the inspection image data with the reference image data, so as to determine whether the inspection image data is abnormal.

A third aspect of the present invention inheres in a method for manufacturing a semiconductor device including executing an inspection processing of an exposure tool including: coating a surface of an inspection target substrate with an inspection resist film; placing a plurality of imaging components deviating from an optical conjugate plane of a surface of the inspection resist film; generating a plurality of inspection patterns of the inspection resist film having a plurality of openings, by projecting exposure beams output from a plurality of effective light sources onto the inspection resist film via the imaging components; measuring one of the inspection patterns as a reference image, and processing the reference image so as to provide reference image data; and determining an abnormal inspection image by measuring inspection images of the inspection patterns and comparing a plurality of inspection image data provided by processing the inspection images with the reference image data; correcting the exposure tool by acquiring a type of defect from the abnormal inspection image when the abnormal inspection image is determined to occur; coating a semiconductor substrate with a manufacturing resist film; loading a manufacturing photomask and the semiconductor substrate to the exposure tool, and subjecting the semiconductor substrate to a manufacturing process of a semiconductor device by delineating the manufacturing resist film using the manufacturing photomask.

DETAILED DESCRIPTION OF THE INVENTION

Figure 1:
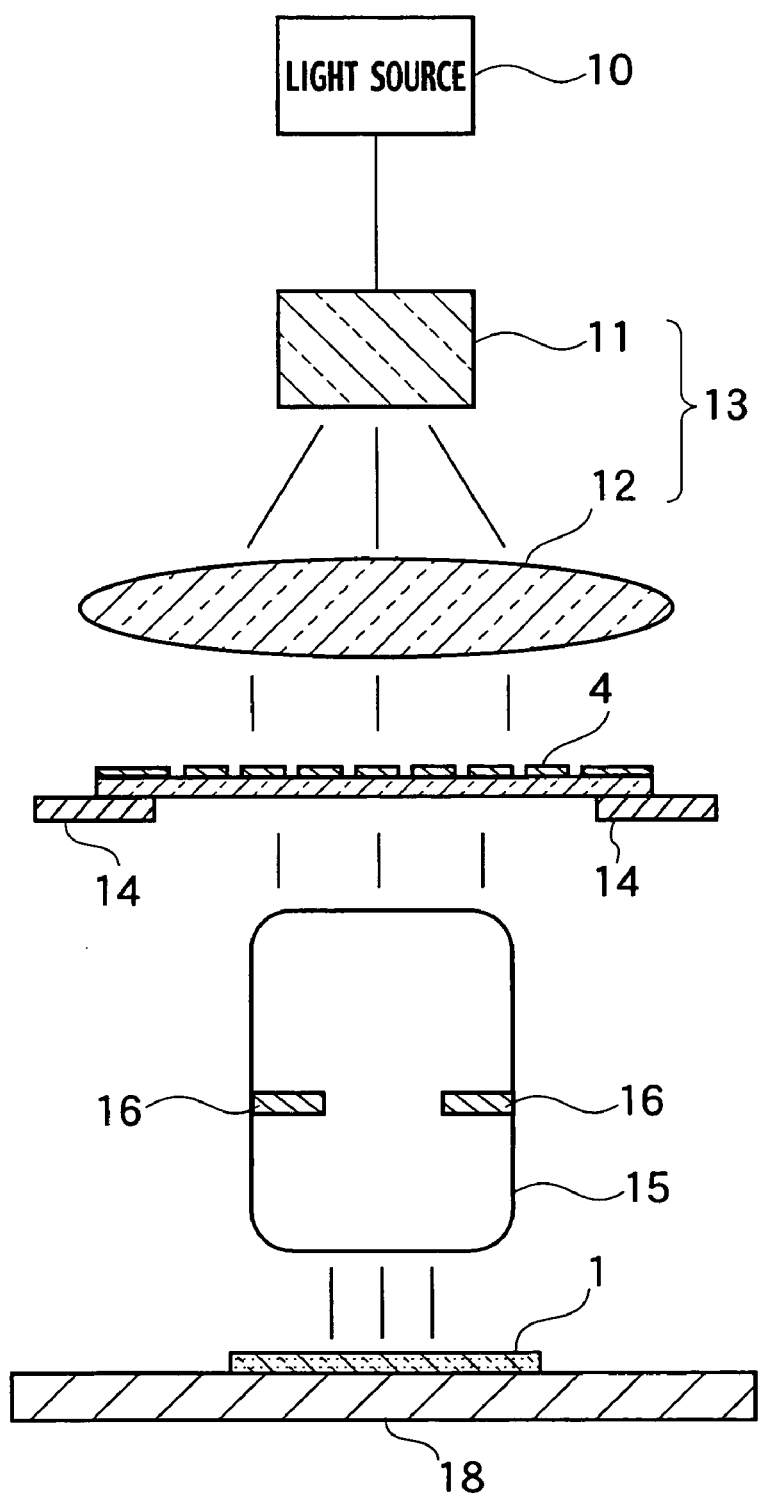
FIG. 1 is a schematic block diagram of an exposure tool for an inspection method according to an embodiment of the present invention.

An embodiment of the present invention will be described with reference to the accompanying drawings. It is to be noted that the same or similar reference numerals are applied to the same or similar parts and elements throughout the drawings, and the description of the same or similar parts and elements will be omitted or simplified.

An exposure tool, which is used for describing an inspection method according to an embodiment of the present invention, is a refracting exposure tool (scanner) as shown in FIG. 1 with a reduction ratio of 1/4. A krypton fluoride (KrF) excimer laser with a wavelength of $\lambda=248$ nm is used as a light source 10. An illumination optical system 13 includes a fly's eye lens 11, a condenser lens 12 and the like. An aperture stop 16 is placed in a projection optical system 15. Exposure beams output from the light source 10 project a semiconductor substrate 1 on a substrate stage 18 via the illumination optical system 13, an inspection photomask 4 placed on a mask stage 14, and a projection optical system 15. Note that the scanner is shown as an exposure tool for convenience of description; alternatively, other than the scanner, a stepper or the like is also applicable. In addition, the reduction ratio is set to 1/4, however, an arbitrary reduction ratio is also permissible. Furthermore, the KrF excimer laser is used as the light source 10, however, another type of excimer laser, such as argon fluoride (ArF), or an ultraviolet light, such as i-line is also available.

Figure 2:
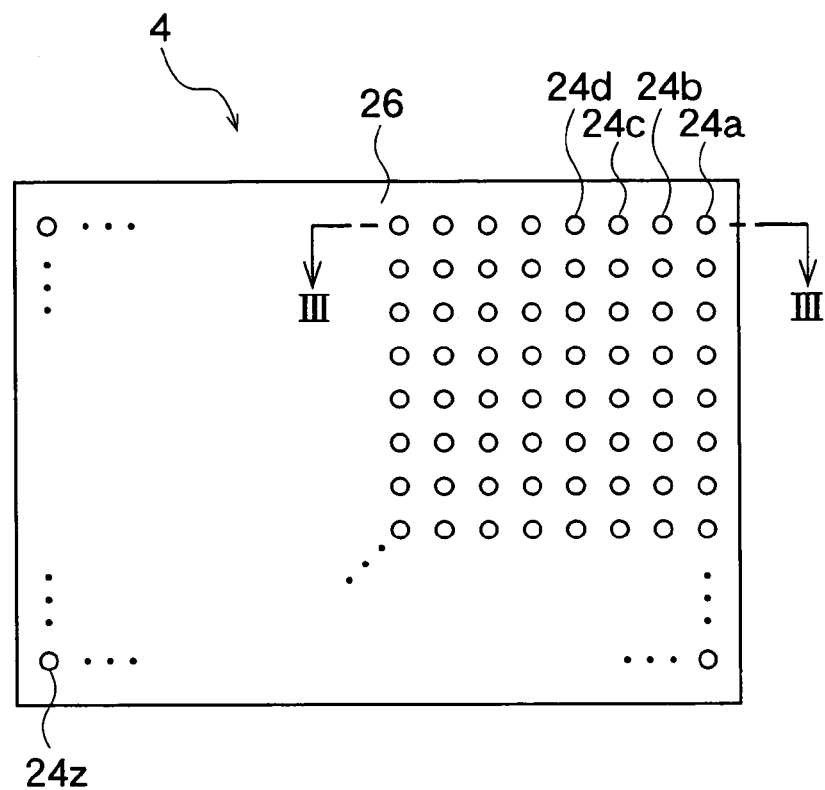
FIG. 2 is a plan view for describing an example of an inspection photomask for the inspection method according to the embodiment of the present invention.
Figure 3:
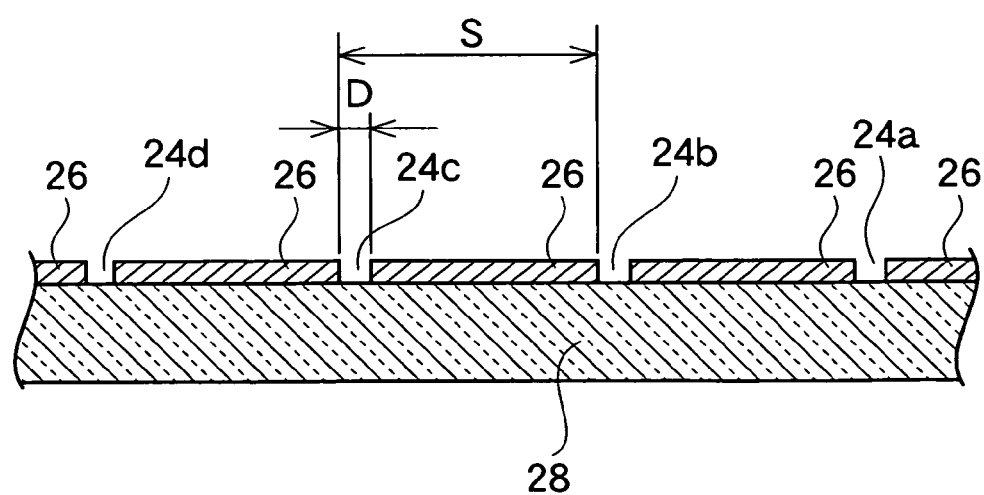
FIG. 3 is a cross-sectional view of the inspection photomask taken along line III-III in FIG. 2.

As shown in FIGS. 2 and 3, the inspection photomask 4 used for describing the inspection method according to the embodiment of the present invention has an opaque film 26 of chromium (Cr), chromium oxide (CrO) or the like, which is provided on a front surface of a transparent substrate 28 such as fused quartz, with a plurality of pinholes (imaging component) 24a, 24b, 24c, 24d, . . . , 24z. For example, the transparent substrate 28 has a thickness of 6.3 mm, and the pinholes 24a, . . . , 24d, . . . , 24z have a diameter D of 55 µm arranged with a pitch S of 500 µm and are provided throughout the entire front surface of a 100×140 mm patterned region of the inspection photomask 4. Naturally, an opaque film is not provided on a rear surface of the transparent substrate 28, facing the front surface on which the opaque film 26 is provided.

Figure 4:
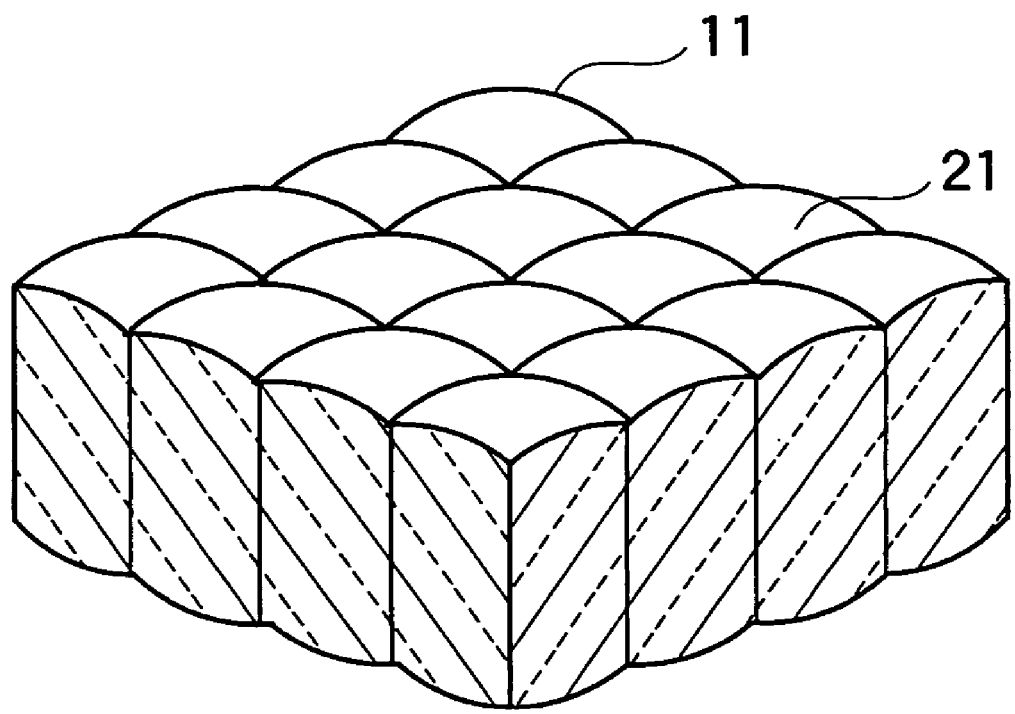
FIG. 4 is a perspective view for describing an example of a fly's eye lens of the exposure tool for the inspection method according to the embodiment of the present invention.
Figure 5:
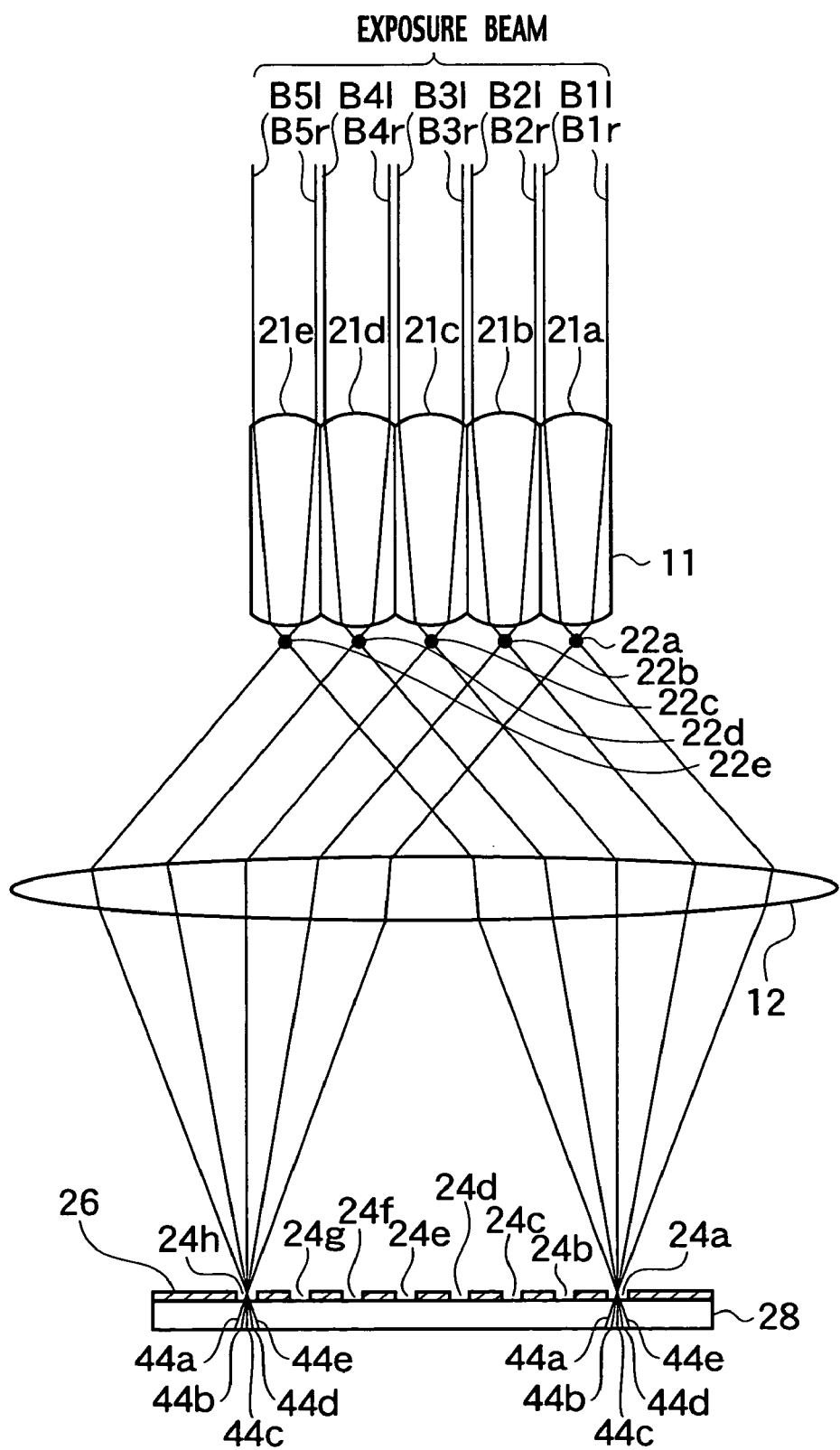
FIG. 5 is a diagram for describing an example of light paths of exposure beams in an illumination optical system for illuminating the inspection photomask for the inspection method according to the embodiment of the present invention.

The fly's eye lens 11 of the illumination optical system 13, which is one of the targets for inspection according to the embodiment of the present invention includes a plurality of rod lenses 21 arranged in a matrix-like shape, as shown in FIG. 4. As shown in FIG. 5, exposure beams output from the light source 10 illuminate the inspection photomask 4 via the fly's eye lens 11 and the condenser lens 12. The inspection photomask 4 is placed such that the front surface having the pinholes 24a through 24h faces the illumination optical system 13. In other words, the front surface of the inspection photomask 4 is deviated from a plane where a pattern of the pinholes 24a through 24h is transferred on a surface of an exposure target substrate (semiconductor substrate) 1, that is, an optical conjugate plane. Therefore, the rear surface of the inspection photomask 4 corresponds to the optical conjugate plane of the semiconductor substrate 1. As a result, images for the pinholes 24a through 24h are not formed on the surface of the semiconductor substrate 1 by the exposure beams. In addition, the diameter D of each of the pinholes 24a, 24d, . . . , 24z is designed so that the exposure beam incident to each of the pinholes 24a, . . . , 24d, . . . , 24z may focus on the rear surface of the transparent substrate 28 of the inspection photomask 4. In other words, the pinholes 24a, . . . , 24d, . . . , 24z function as an imaging component for a pinhole camera.

For example, as shown in FIG. 5, the exposure beams incident to the right and the left edge of a cross section of the rod lens 21a of the fly's eye lens 11 are provided as B1r and B1l, respectively; exposure beams incident to the right and the left edge of a cross section of the rod lens 21b are provided as B2r and B2l, respectively; the same for the rod lens 21c are provided as B3r and B3l, respectively; the same for the rod lens 21d are provided as B4r and B4l, respectively; and the same for the rod lens 21e are provided as B5r and B5l, respectively. Each of the exposure beams B1r, B1l, B2r, B2l, B3r, B3l, B4r, B41, B5r, and B51 incident to the fly's eye lens 11 is gathered by the rod lenses 21a through 21e, forming effective light sources 22a, 22b, 22c, 22d, and 22e as point sources, respectively, on the output side of the fly's eye lens 11. The exposure beams B1r, B1l, B2r, B2l, B3r, B3l, B4r, B4l, B5r, and B5l passed through the effective light sources 22a through 22e, respectively, are refracted by the condenser lens 12, and enter any one of the pinholes 24a through 24h of the inspection photomask 4. For example, the exposure beams B1l, B2l, B3l, B4l, and B5l incident to the left edges of the rod lenses 21a through 21e, respectively, enter the pinhole 24a at the right edge of the inspection photomask 4, so as to form effective light source images 44a through 44e on the rear surface of the transparent substrate 28 of the inspection photomask 4. On the other hand, the exposure beams B1r, B2r, B3r, B4r, and B5r incident to the right edges of the rod lenses 21a through 21e, respectively, enter the pinhole 24h at the left edge of the inspection photomask 4, so as to form the effective light source images 44a through 44e on the rear surface of the transparent substrate 28 of the inspection photomask 4. Similarly, the exposure beams incident to intermediate regions ranging from the left to the right edges of the respective rod lenses 21a through 21e enter any one of the pinholes 24b through 24g, which are placed at the intermediate regions ranging from the right to the left edge of the inspection photomask 4 corresponding to incident positions, by the condenser lens 12, so as to form the effective light source images 44a through 44e on the rear surface of the transparent substrate 28 of the inspection photomask 4, respectively. In the embodiment of the present invention as described above, the exposure beams allow formation of the effective light source images 44a through 44e on the rear surface of the transparent substrate 28 of the inspection photomask 4 using the pinholes 24a through 24h of the inspection photomask 4 as lenses. More specifically, the rear surface of the inspection photomask 4 is optically conjugated for the effective light sources 22a through 22e. Accordingly, the exposure beams passing through the pinholes 24a through 24h of the inspection photomask 4 may reduce and project the effective light source images 44a through 44e of the effective light sources 22a through 22e, which are formed by the fly's eye lens 11, by the projection optical system 15, on the surface of the semiconductor substrate 1 that is optically conjugated for the rear surface of the transparent substrate 28 of the inspection photomask 4 and the effective light sources 22a through 22e.

Figure 6:
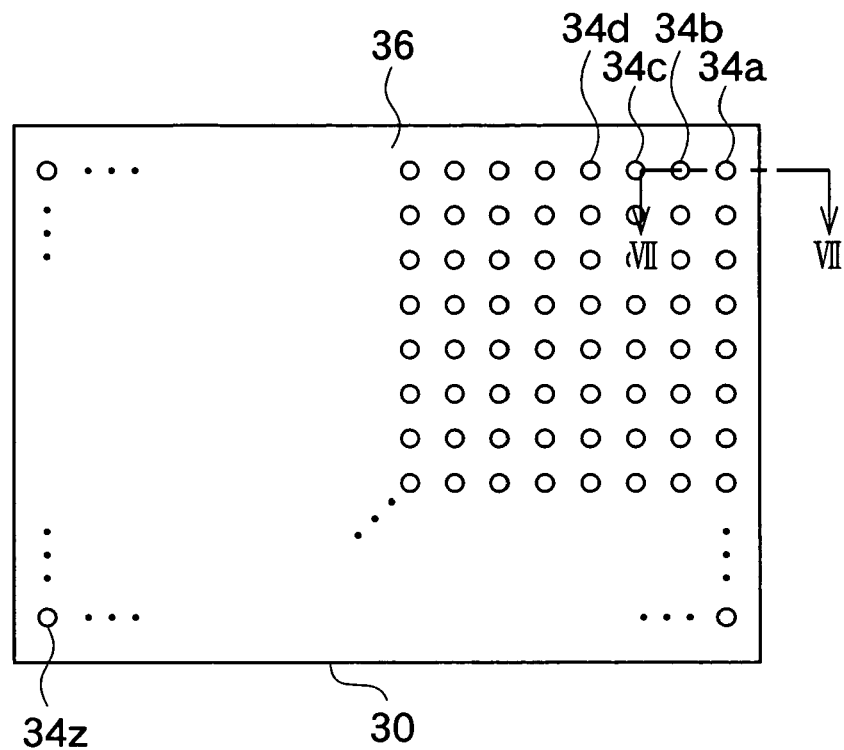
FIG. 6 is a plan view for describing an example of an inspection pattern transferred onto a semiconductor substrate from the inspection photomask for the inspection method according to the embodiment of the present invention.
Figure 7:
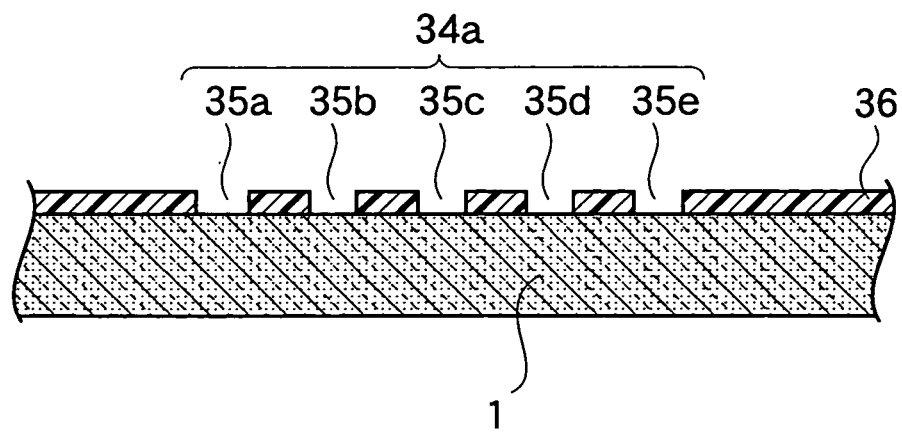
FIG. 7 is a cross-sectional view of the inspection pattern transferred onto the semiconductor substrate taken along line VII-VII in FIG. 6.
Figure 8:
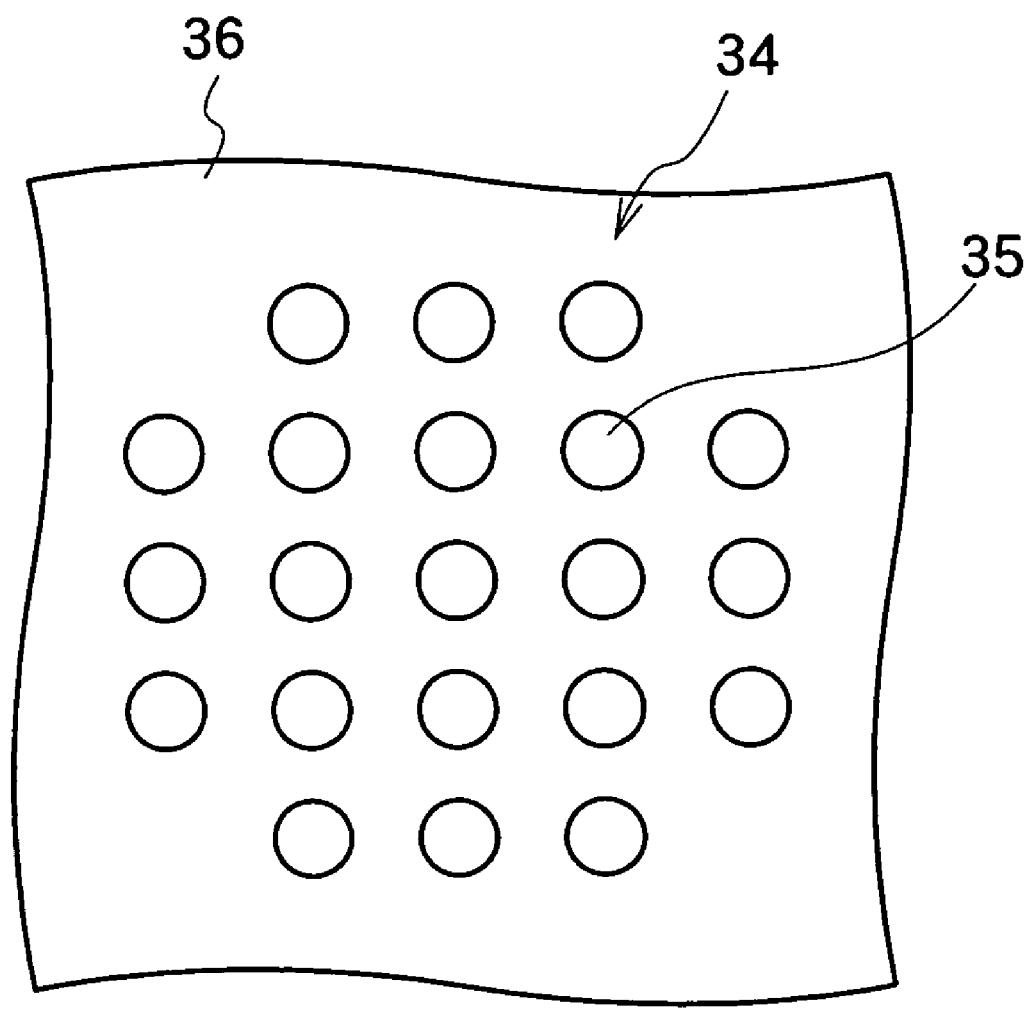
FIG. 8 is a view for describing an example of a shape of the inspection pattern transferred onto the semiconductor substrate from the inspection photomask for the inspection method according to the embodiment of the present invention.

For example, a positive photoresist is coated on the surface of the semiconductor substrate 1. Then the surface of the semiconductor substrate 1 is exposed with the configuration shown in FIGS. 1 and 5. After development, as shown in FIG. 6, the effective light source images 44a through 44e of the effective light sources 22a through 22e are reduced and projected to an exposure field 30 of a resist film 36 on the surface of the semiconductor substrate 1 corresponding to the positions of the pinholes 24a, 24b, . . . , 24z of the inspection photomask 4. Thus, inspection patterns 34a, 34b, 34c, 34d, . . . , 34z of the resist film 36 are generated. For example, in a cross-section of the inspection pattern 34a taken along line VII-VII in FIG. 6, as shown in FIG. 7, a plurality of openings 35a through 35e corresponding to the plurality of effective light sources 22a through 22e, respectively, are formed. Therefore, as shown in FIG. 8, for example, an inspection pattern 34 including a plurality of openings 35, which are two-dimensionally arranged corresponding to the rod lens 21 of the fly's eye lens 11, is formed on the resist film 36.

Figure 9:
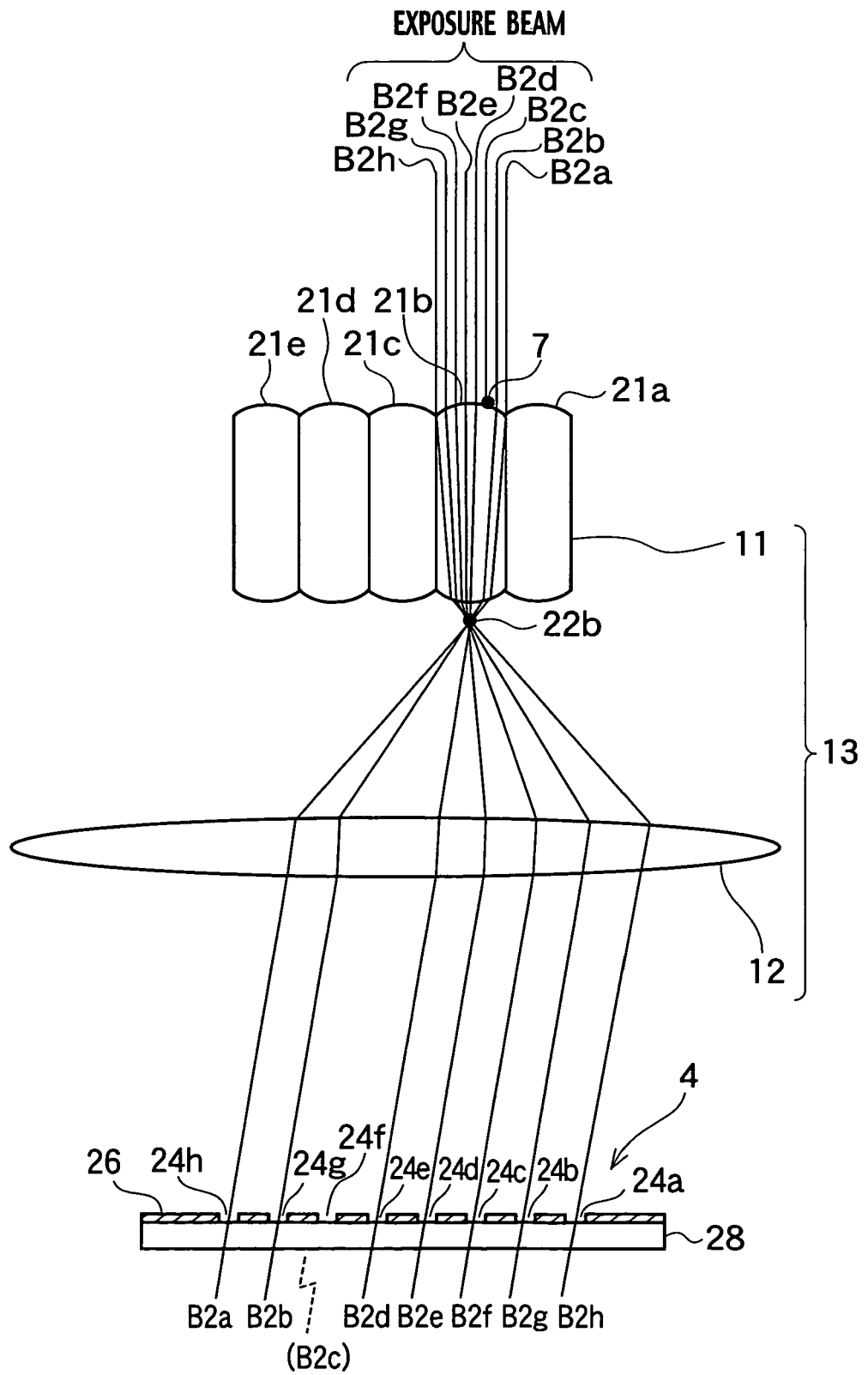
FIG. 9 is a diagram for describing an example of light paths of the exposure beams in the illumination optical system with a local defect, illuminating the inspection photomask according to the embodiment of the present invention.
Figure 10:
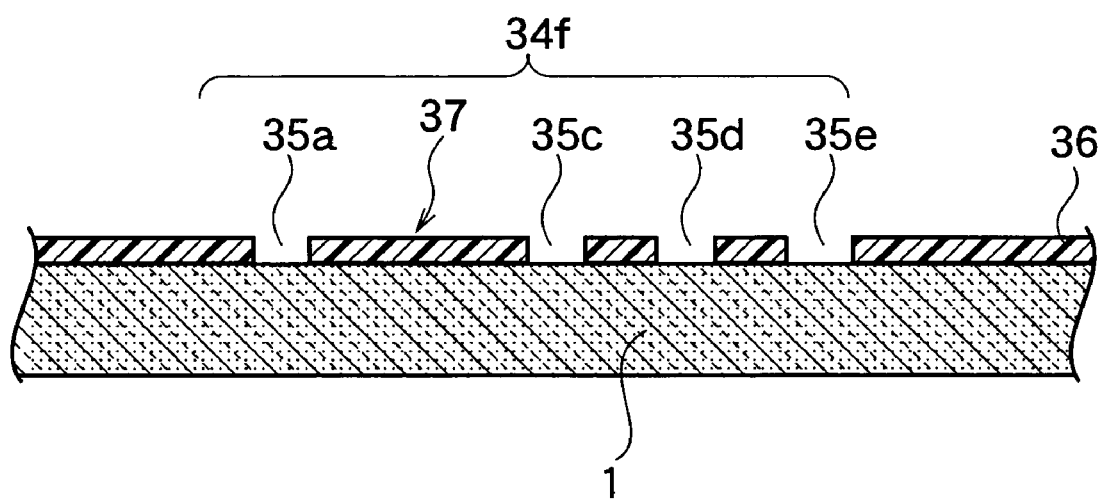
FIG. 10 is a cross-sectional view for describing an example of an inspection pattern generated onto the semiconductor substrate through the illumination optical system with a local defect from the inspection photomask for the inspection method according to the embodiment of the present invention.

Next, a case of the illumination optical system 13 having a local defect is described below. As shown in FIG. 9, a defect 7, such as dust, is on a surface of the rod lens 21b facing the light source 10 shown in FIG. 1, among the rod lenses 21a through 21e in the fly's eye lens 11, for example. Exposure beams B2a through B2h incident to the rod lens 21b enter the pinholes 24a through 24e of the inspection photomask 4 via the illumination optical system 13. In this case, as shown in FIG. 9, the exposure beams B2a through B2h are incident to the condenser lens 12 being reversed mirror from side to side about the effective light source 22b, respectively. Thus, the exposure beam B2a is incident to the pin hole 24h, and the exposure beam B2b is incident to the pinhole 24g. Similarly, the exposure beams B2d through B2h are incident to the pinhole 24e through 24a. Since the position of the defect 7 is the incident position of the exposure beam B2c, the exposure beam B2c may not transmit to the rod lens 21b. Accordingly, exposure beam B2c is not incident to the pinhole 24f via the rod lens 21b. As a result, as shown in FIG. 10, openings 35a, 35c, 35d, and 35e corresponding to the effective light sources 22a, 22c, 22d, and 22e, respectively, are formed in the inspection pattern 34f of the resist film 36 corresponding to the pinhole 24f, while a defect image 37 without an opening is formed at a position corresponding to the effective light source 22b. Note that in the above description, the position of the defect 7 is on the surface of the incident side of the fly's eye lens 11. Alternatively, the position of the defect 7 may be on a surface of the output side of the fly's eye lens 11 or on a surface of the condenser lens 12. In addition, as the defect 7, not only the dust but also anything that can change the light path of the exposure beam, such as a scratch occurred on the fly's eye lens 11 or the condenser lens 12, may form a similar defect image. Furthermore, the case of a local defect 7 of the illumination optical system 13 being transferred to a single inspection pattern 34f is described. Alternatively, depending on the size of the local defect 7, defect images may be transferred to a plurality of inspection patterns. For example, if the defect covers the entire rod lens 21b, the effective light source 22b is not formed. Therefore, the effective light sources 22a through 22e excluding the effective light source 22b are projected. As a result, a common defect is transferred to all inspection patterns.

Figure 11:
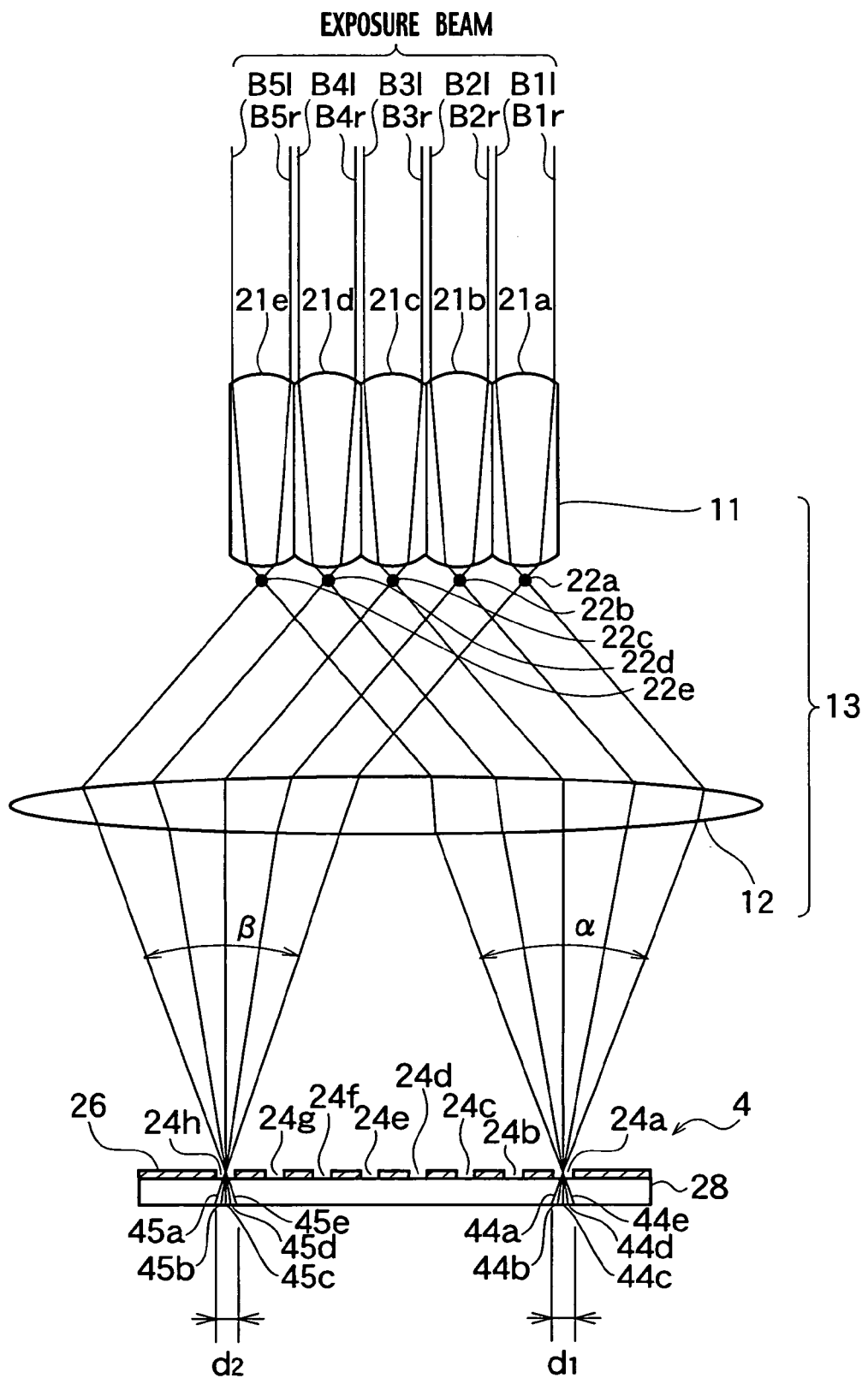
FIG. 11 is a diagram for describing an example of light paths of exposure beams in the illumination optical system with a local defect, illuminating the inspection photomask according to the embodiment of the present invention.
Figure 12:
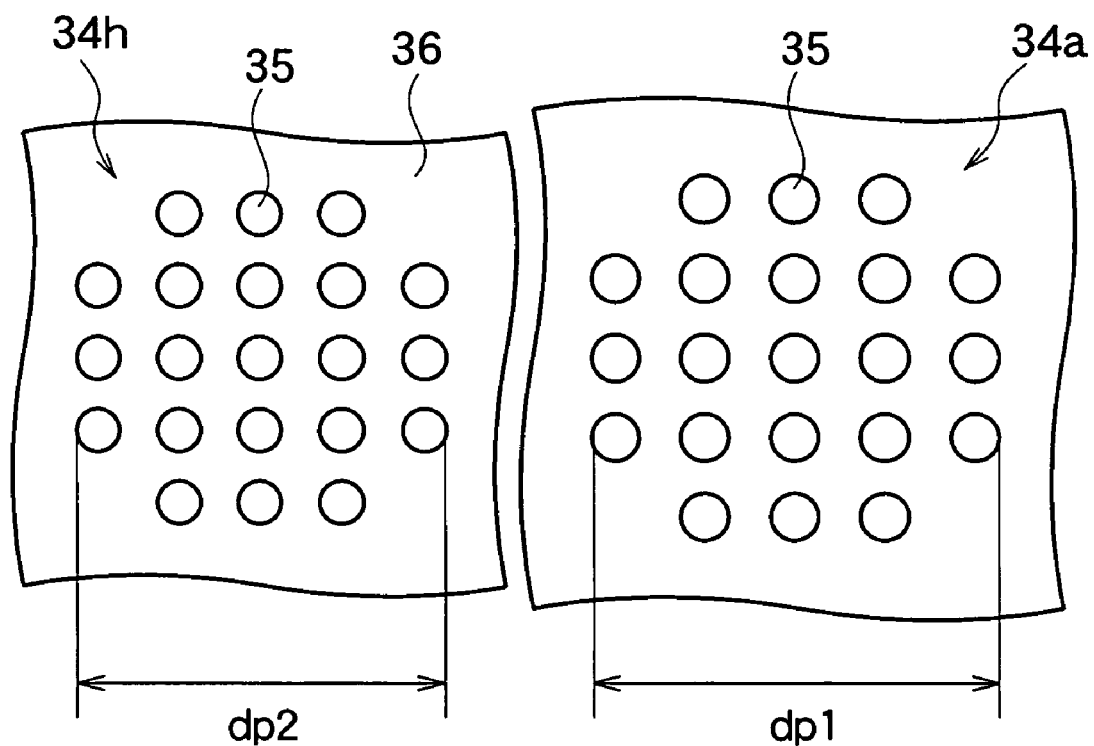
FIG. 12 is a view for describing another example of an inspection pattern transferred onto the semiconductor substrate through the illumination optical system with a local defect from the inspection photomask for the inspection method according to the embodiment of the present invention.

In addition, when the condenser lens 12 has an aberration, a light path of the exposure beam may vary, and the effective light source image to be projected onto the semiconductor substrate 1 may also vary. For example, as shown in FIG. 11, the condenser lens 12 has a local aberration on the left side. The exposure beams Blr, B1l, B2r, B2l, B3r, B3l, B4r, B4l, B5r, and B5l incident to the fly's eye lens 11 are gathered by the rod lenses 21a through 21e, respectively, forming the effective light sources 22a through 22e on the output side of the fly's eye lens 11. The exposure beams B1l, B2l, B3l, B4l, and B5l passing through the effective light sources 22a through 22e are incident to the pinhole 24a of the inspection photomask 4 with an incident angle α via the condenser lens 12. On the other hand, light paths for the respective exposure beams B1r, B2r, B3r, B4r, and B5r are abnormally diffracted due to the aberration of the condenser lens 12, and are incident to the pinhole 24h of the inspection photomask 4 with an incident angle β, which is smaller than the incident angle α. As a result, as shown in FIG. 11, a diameter d2 of a pattern formed by the effective light source images 45a through 45e corresponding to the pinhole 24h is smaller than a diameter d1 of a pattern formed by the effective light source images 44a through 44e corresponding to the pinhole 24a, which are formed via a normal region of the condenser lens 12 where there is no aberration. The effective light source images 44a through 44e and 45a through 45e, which are formed by the beams passing through the pinholes 24a and 24h, are reduced and projected onto the resist film 36 by the projection optical system 15, generating the inspection patterns 34a and 34h having a plurality of openings 35, as shown in FIG. 12. The inspection patterns 34a and 34h have diameters dp1 and dp2, respectively, corresponding to the diameters d1 and d2 of the patterns of the effective light source images 44a through 44e and 45a through 45e according to the reduction ratio of the exposure tool. Consequently, the diameter dp2 of the inspection pattern 34h is smaller by a difference Δdp than the diameter dp1 of the normal inspection pattern 34a. In this manner, the local aberration of the condenser lens 12 may form a defect image, which has a variation in the shape of the inspection pattern 34h delineated to the resist film 36.

As described above, the case of a local defect of the illumination optical system 13 being transferred to a single inspection pattern is described. Alternatively, depending on the size of the local defect, the defect may be transferred to a plurality of inspection patterns. In addition, although the transferred defect 37 shown in FIG. 10 or the difference Δdp in the diameter of the effective light source image is minute, it can be observed by an optical microscope. Nevertheless, since several tens of thousands of pinholes 24a, 24b, . . . , 24z are actually arranged on the inspection photomask 4, it is difficult and time consuming to sequentially examine the several tens of thousands of inspection patterns 34a, 34b, . . . , 34z delineated to the resist film 36 so as to extract the minute defect image 37, the inspection pattern 34f having the minute defect image 37, or the inspection pattern 34h having the variation Δdp in the diameter of the effective light source image.

According to the embodiment of the present invention, the plurality of pinholes 24a, 24b, . . . , 24z in the inspection photomask 4 are placed so as to deviate from the optical conjugate plane of the resist film 36 on the surface of the semiconductor substrate 1. The effective light sources 22a through 22e, which are formed by the illumination optical system 13 of the exposure tool, are then transferred to generate the plurality of inspection patterns 34a, 34b, . . . , 34z on the resist film 36 corresponding to the pinholes 24a, 24b, . . . , 24z, respectively. One of the inspection patterns 34a, 34b, . . . , 34z is measured as a reference image and is then subjected to an image processing to obtain reference image data. In addition, a plurality of inspection image data, which are obtained by image processing measured inspection images of the plurality of inspection patterns 34a, 34b, . . . , 34z, are compared with the reference image data. The inspection image data include, for example, brightness of the inspection image of the inspection pattern, a shape including the diameter of the inspection image of the inspection pattern, and the like. For example, when a normal inspection pattern is selected as a reference image, inspection image data significantly different from the reference image data is determined as being abnormal. On the other hand, when an abnormal inspection pattern is used as a reference image, most inspection image data are determined to be significantly different. Therefore, a small number of inspection image data not significantly different from the reference image data should be determined as being abnormal. In this manner, according to the embodiment of the present invention, the inspection pattern 34f having the minute defect image 37, the inspection pattern 34h having the variation Δdp in the diameter of the effective light source image can be easily detected. Moreover, even when all of the inspection image data is determined as being normal, all images may include a common defect. In such case, whether or not a common defect occurs is determined by inspecting one of the inspection images or the reference image.

Figure 13:
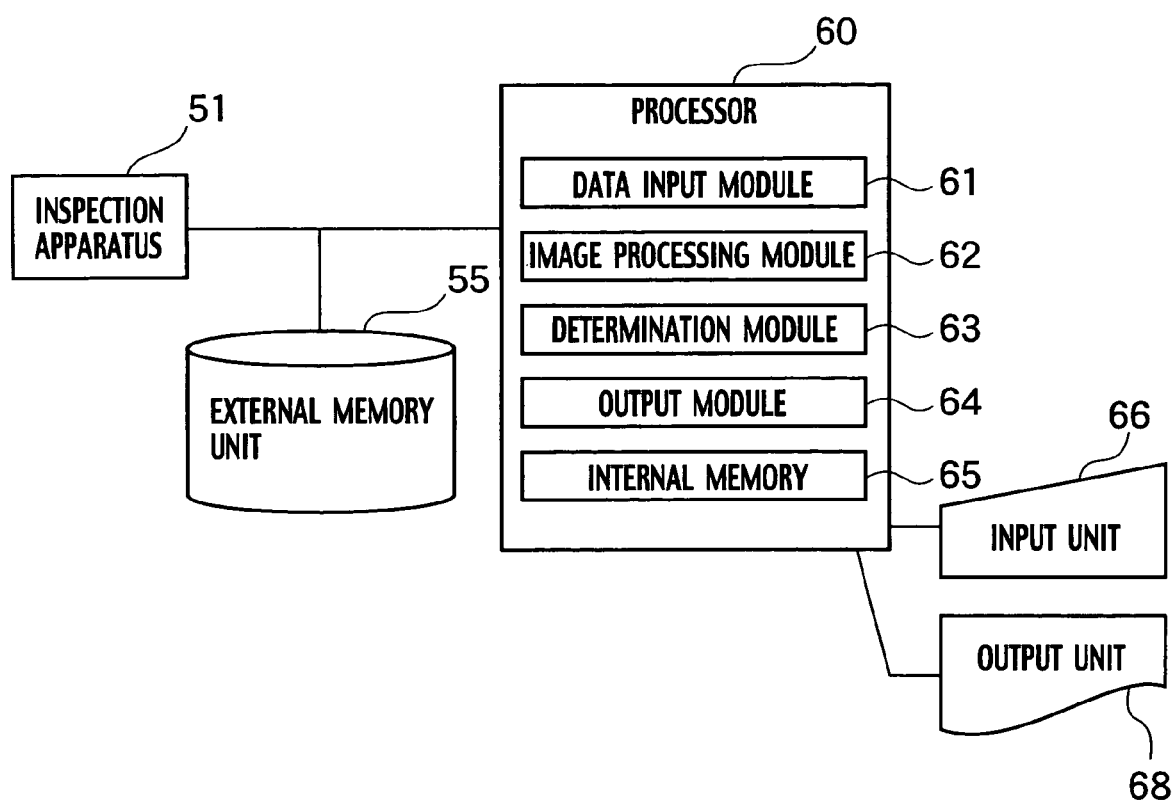
FIG. 13 is a diagram for describing a schematic configuration of an inspection system according to the embodiment of the present invention.

As shown in FIG. 13, an inspection system used for an inspection method according to the embodiment of the present invention includes an inspection apparatus 51, which optically measures an inspection pattern and converts the measured resist pattern to an image, a processor 60, which acquires the image measured by the inspection apparatus 51 and subjects the image to an image processing, and an external memory unit 55, which stores information, such as an image output from the inspection apparatus 51 and image data processed by the processor 60. In addition, an input unit 66 and an output unit 68 are connected to the processor 60.

The input unit 66 refers to instruments such as a keyboard, a mouse and the like. When an input operation is performed by the input unit 66, corresponding key information is transmitted to the processor 60. The output unit 68 refers to a screen such as a monitor or the like, a liquid crystal display (LCD), a light-emitting diode (LED) panel, an electroluminescence (EL) panel and the like.

The inspection apparatus 51, for example, illuminates an inspection pattern delineated to the resist film 36 on the semiconductor substrate 1 using an illumination apparatus, so as to focus the reflected light from the inspection pattern on a photoelectric transfer device such as a charge coupled device (CCD) by a detection optical system including an imaging lens. Furthermore, the inspection apparatus 51 converts an electric signal detected by the photoelectric transfer device to an image.

The processor 60 has a data input module 61, which acquires a reference image and an inspection image of an inspection pattern delineated onto the resist film 36 from the inspection apparatus 51, an image processing module 62, which calculates reference image data and inspection image data from the reference image and the inspection image, a determination module 63, which determines whether or not the inspection image data is abnormal by comparing the reference image data and the inspection image data, an output module 64, which outputs a determination result as an inspection data file, and an internal memory 65, which stores the inspection data file. The processor 60 may be provided by a central processing unit (CPU) used for a computer. Note that the inspection data file may be stored in the external memory unit 55. In such manner, with the inspection system according to the embodiment of the present invention, since the processor 60 provided by the CPU automatically detects the inspection pattern 34f having the minute defect image 37 or the inspection pattern 34h having the variation Δdp in the diameter of the effective light source, inspection processing for the illumination optical system 13 can be implemented within a short time.

Figure 14:
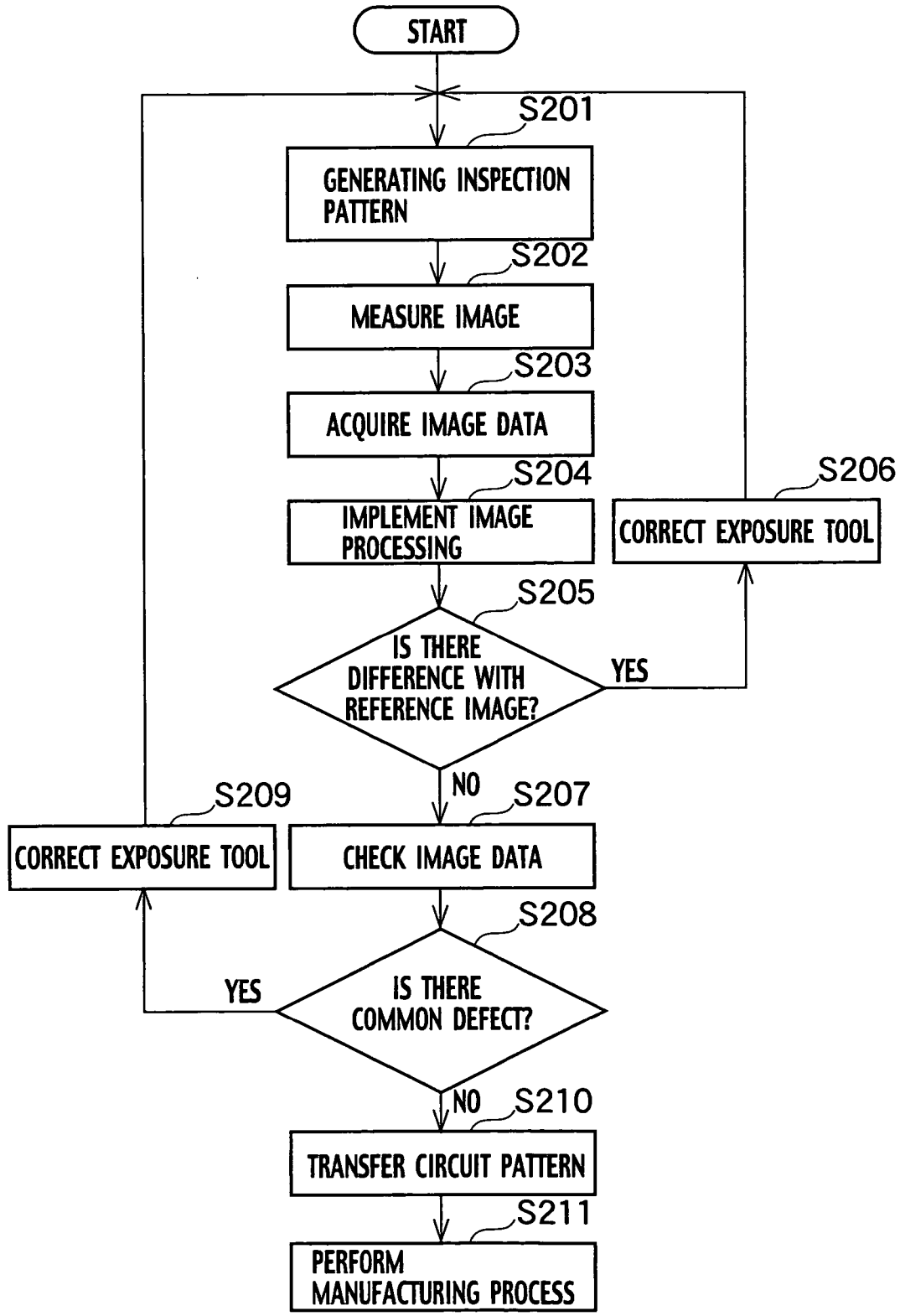
FIG. 14 is a flow chart for describing the inspection method according to the embodiment of the present invention.

Next, an inspection method according to the embodiment of the present invention is described below with reference to a flowchart shown in FIG. 14.

Figure 15:
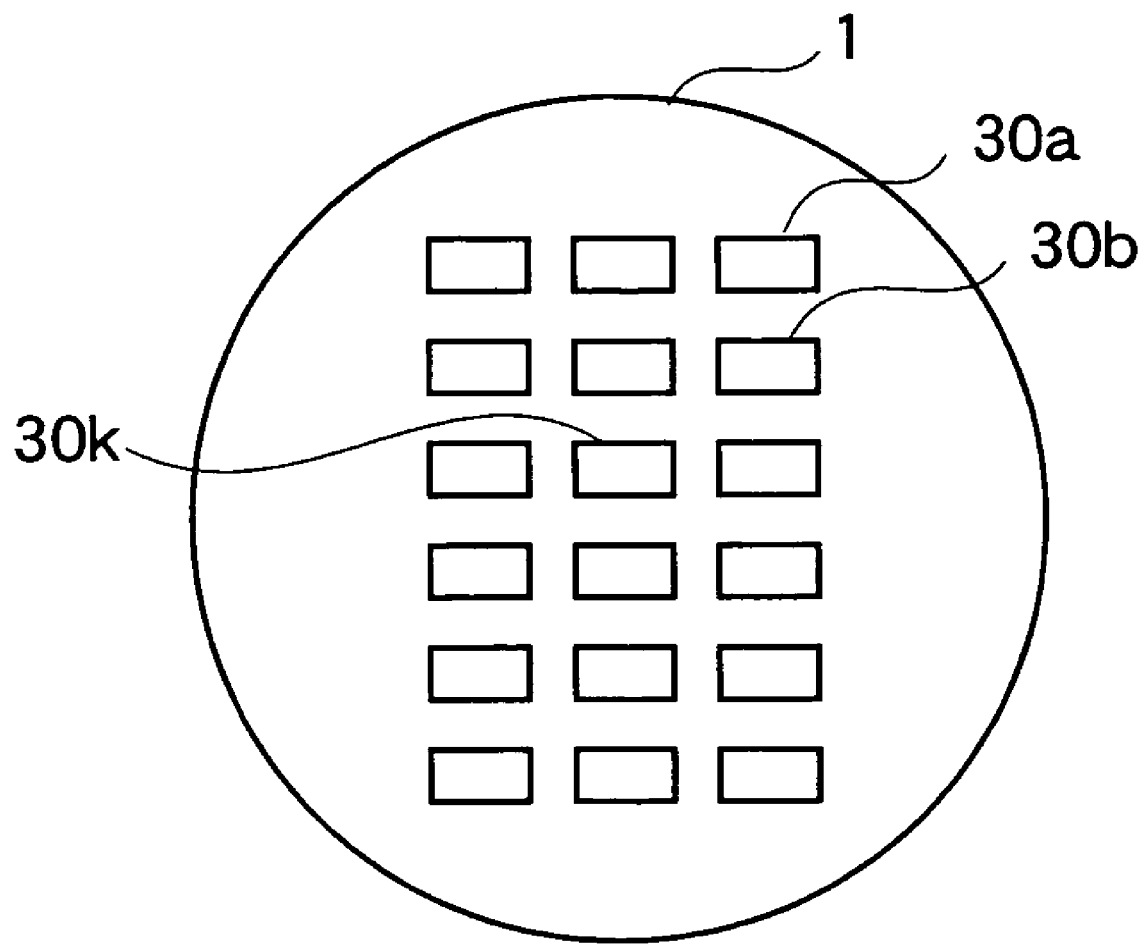
FIG. 15 is a view for describing an example of an exposure field on the semiconductor substrate for the inspection method according to the embodiment of the present invention.

(a) To begin with, in Step S201, a resist film 36 is coated on a surface of an inspection target substrate (semiconductor substrate) 1, and the semiconductor substrate 1 is then loaded to the exposure tool shown in FIG. 1. The inspection photomask 4 shown in FIG. 2, having a front surface in which a plurality of pinholes 24a through 24z are arranged, is placed so as to deviate the front surface of the inspection photomask 4 from the optical conjugate plane of the surface of the resist film 36. By projecting each exposure beam output from the plurality of effective light sources 22a through 22e to the resist film 36 via the plurality of pinholes 24a through 24z, a plurality of inspection patterns 34a through 34z having a plurality of openings aregenerated. As shown in FIG. 15, by using a one-shot static exposure method, the inspection photomask 4 is sequentially exposed to each of a plurality of exposure fields 30a, 30b, . . . , 30k, . . . , on the resist film 36 coated on the surface of the semiconductor substrate 1, with changing exposure doses, respectively. After development of the exposed semiconductor substrate 1, transferred images are observed using an optical microscope, and the most appropriate exposure field is selected for inspection.

(b) Next, in Step S202, the semiconductor substrate 1 is loaded in the inspection apparatus 51 in FIG. 13, and the images of the inspection patterns 34a, 34b, . . . in the selected exposure field are measured.

(c) In Step S203, the data input module 61 in the processor 60 acquires images from the inspection apparatus 51.

(d) In Step 204, the image processing module 62 selects one of the images acquired from the input module 61, as a reference image, and other images as inspection images. By image processing of the reference image and the inspection images, reference image data and inspection image data including such data as brightness, shape and the like are created.

(e) In Step S205, the determination module 63 compares the inspection image data with the reference image data in order to determine whether or not there is abnormal inspection image data that shows a significant difference.

(f) If it is determined that there is abnormal inspection image data, the illumination optical system 13 of the exposure tool is corrected based on a defect image of the abnormal inspection image in Step S206, and then inspection processing is repeated from Step S201.

(g) On the contrary, if it is determined that there is no abnormal inspection image data, one of the reference image and the inspection images is checked in Step S207. Then, in Step S208, it is determined whether or not a common defect occurs.

(h) If it is determined that a common defect has occurred, in Step S209, the illumination optical system 13 of the exposure tool is corrected based on the checked result of the image, and then inspection processing is repeated from Step S201.

(i) On the contrary, if it is determined that there is not either of a defect image nor a common defect in the inspection image, inspection processing of the illumination optical system 13 of the exposure tool ends. Consequently, the exposure tool is available for a manufacturing process of a semiconductor device. For example, in Step S210, a circuit pattern is transferred onto the resist film of the semiconductor substrate for manufacturing the semiconductor device. In Step S211, a manufacturing process of the semiconductor device is implemented using the transferred circuit resist pattern as a mask.

In the inspection method according to the embodiment of the present invention, since the processor 60 automatically detects the inspection pattern 34f having the minute defect image 37 or the inspection pattern 34h having the variation Δdp in the diameter of the effective light source, by comparing the inspection image data with the arbitrarily selected reference image data, inspection processing of the illumination optical system 13 can be implemented within a short time.

In addition, with the inspection method according to the embodiment of the present invention, the inspection patterns 34a through 34z having the openings 35a through 35e, which are transferred images of the effective light sources 22a through 22e formed by the illumination optical system 13, are subjected to inspection, inspection processing for a local defect of the illumination optical system 13 which can be directly implemented.

(First Modification)

Figure 16:
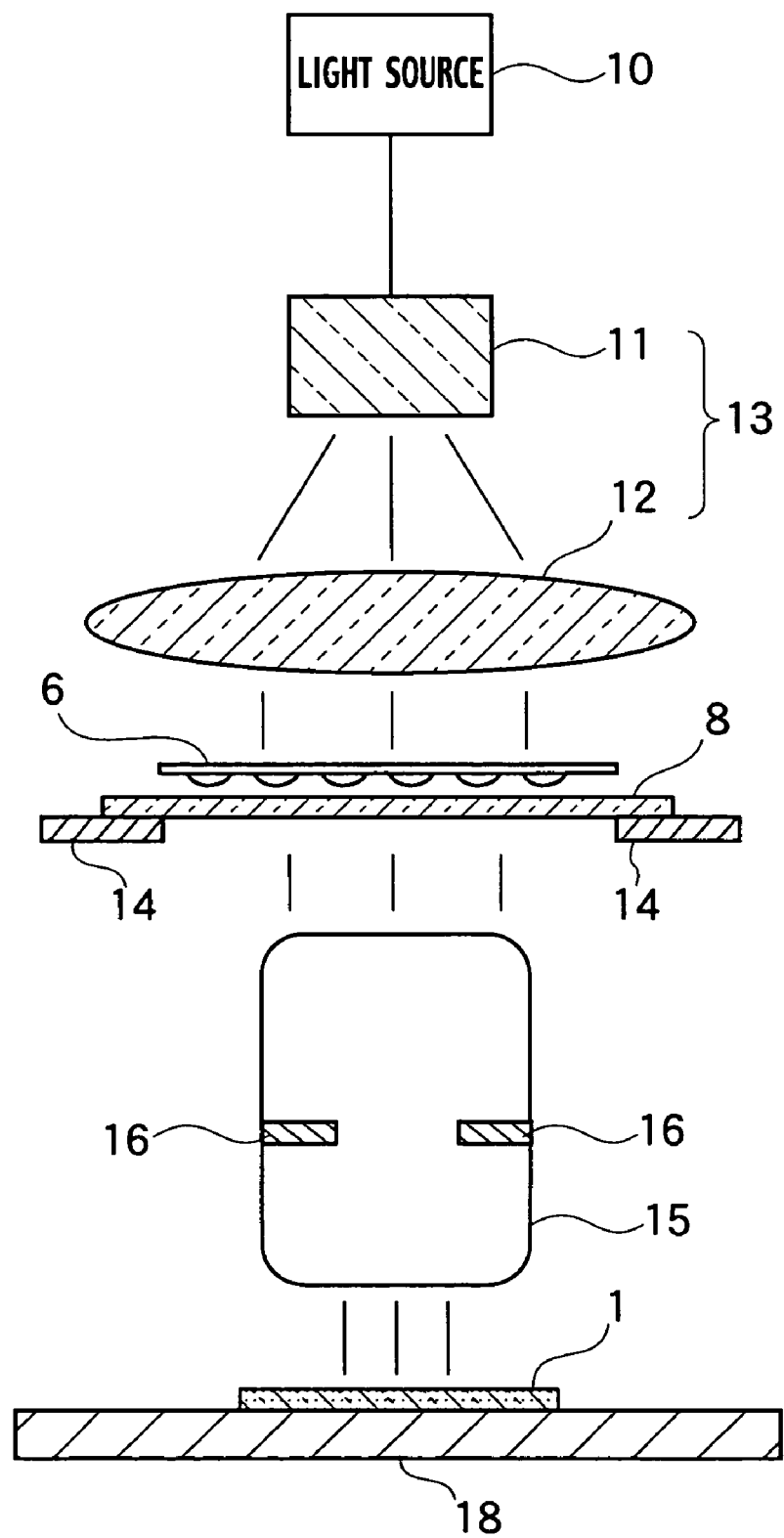
FIG. 16 is a schematic block diagram of an exposure tool for an inspection method according to a first modification of the embodiment of the present invention.

As shown in FIG. 16, an inspection method according to a first modification of the embodiment of the present invention uses a lens array 6 as an imaging component instead of pinholes arranged on a front surface of an inspection photomask. A transparent substrate 8 which does not have an opaque film is placed on a mask stage 14 in place of the inspection photomask. The lens array 6 is placed between the transparent substrate 8 and the illumination optical system 13. Since the first modification of the embodiment of the present invention is the same as the embodiment of the present invention except for the lens array 6 used in place of the pinholes, duplicate description is omitted.

Figure 17:
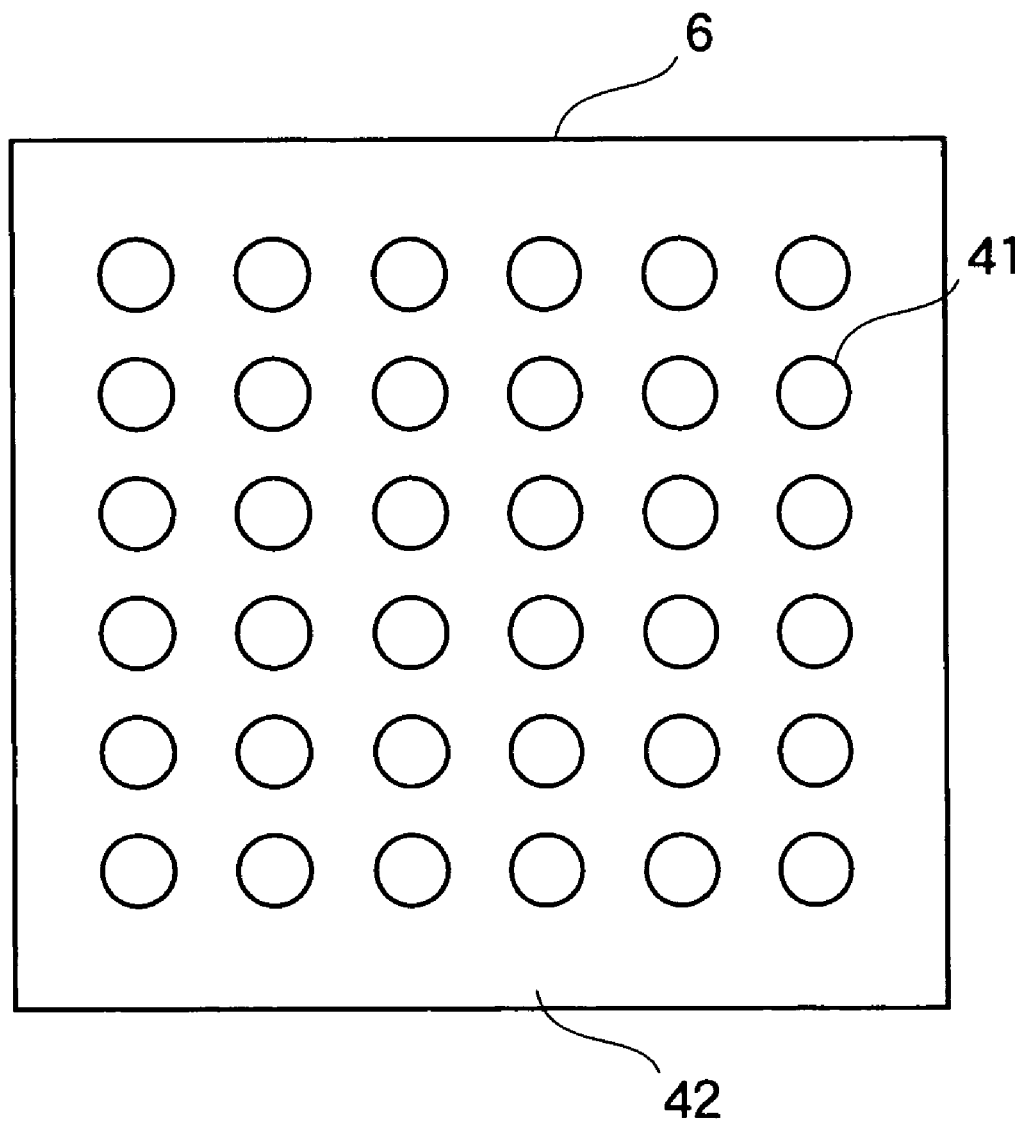
FIG. 17 is a plan view for describing an example of a lens array for the inspection method according to the first modification of the embodiment of the present invention.

As shown in FIG. 17, the lens array 6 according to the first modification of the embodiment of the present invention has a plurality of lenses 41, which are two-dimensionally and periodically arranged on a surface of a lens support substrate 42, which is made of a transparent material such as fused quartz. The lens array 6 is placed at a plane that is deviated from the optical conjugate plane of the surface of the semiconductor substrate 1 so that the plurality of lenses 41 focus on the optical conjugate plane of the surface of the semiconductor substrate 1. Accordingly, positions of effective light sources of the illumination optical system 13 and the focal positions of the plurality of lenses 41 are optically conjugated, and a plurality of images of the effective light sources are projected onto the surface of the semiconductor substrate 1 by the plurality of lenses 41, respectively. Thus, use of the inspection pattern delineated onto the resist film of the semiconductor substrate 1 allows detection of a local defect of the illumination optical system 13 in the exposure tool.

According to the inspection method of the first modification of the embodiment of the present invention, inspection processing for a local defect of the illumination optical system can be easily implemented within a short time.

(Second Modification)

Figure 18:
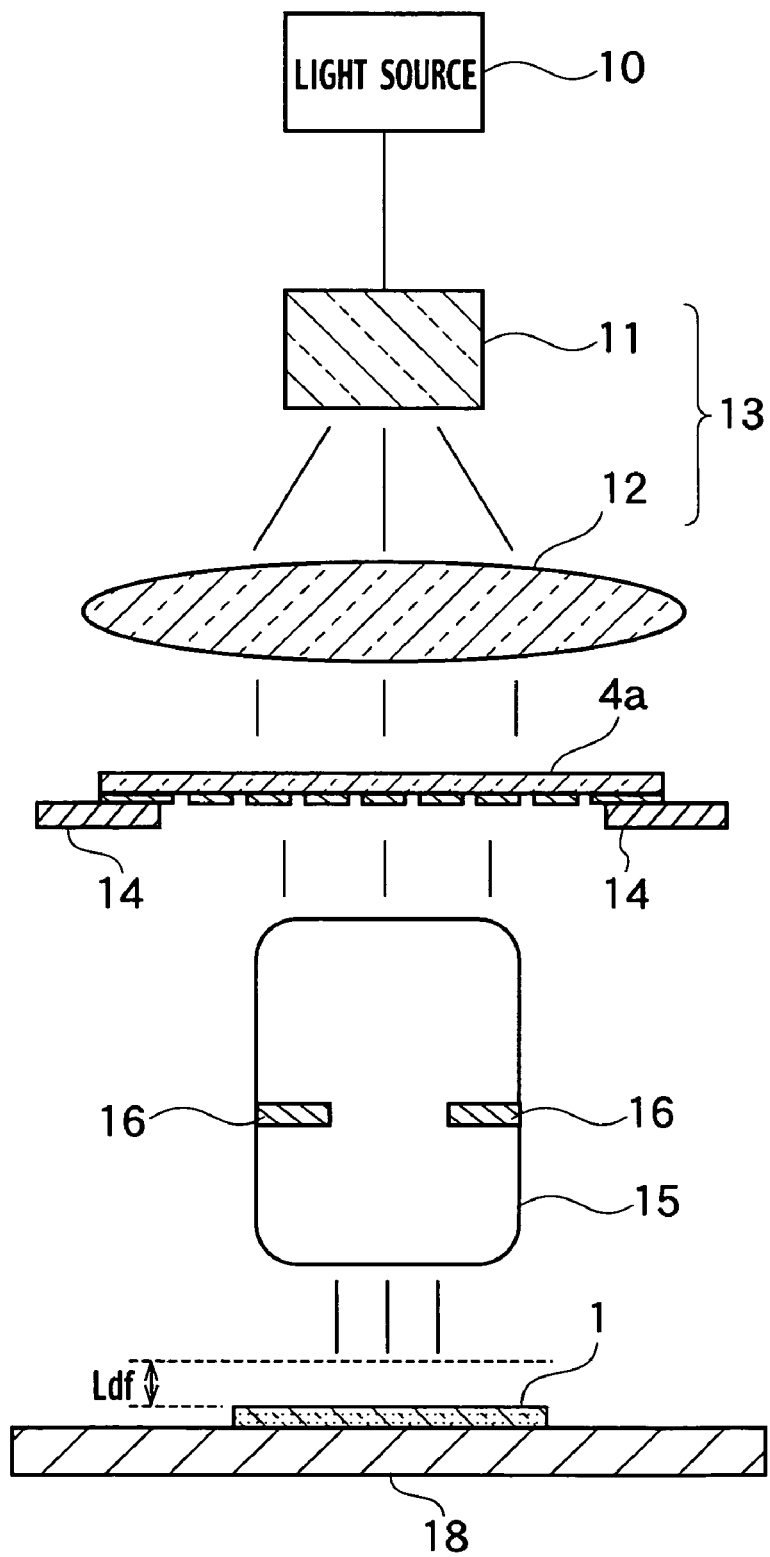
FIG. 18 is a schematic block diagram of an exposure tool for an inspection method according to a second modification of the embodiment of the present invention.

As shown in FIG. 18, according to an inspection method of a second modification of the embodiment of the present invention, an inspection photomask 4a is placed so that a plurality of pinholes on the front surface of the photomask 4a face the projection optical system 15. The semiconductor substrate 1 placed on the substrate stage 18 is moved downwardly by a distance Ldf so that the surface of the semiconductor substrate 1 deviates from the optical conjugate plane of the front surface of the inspection photomask 4a in which the pinholes are arranged. According to the second modification of the embodiment of the present invention, the positions of the inspection photomask 4a and the semiconductor substrate 1 are different from the positions of the embodiment of the present invention. Since other elements are the same, duplicate descriptions are omitted.

The inspection photomask 4a used for the inspection method according to the second modification of the embodiment of the present invention has a plurality of pinholes arranged in an opaque film having a diameter D of 3 μm arranged with a pitch S of 30 μm throughout the entire front surface of a 100×140 mm patterned region of the inspection photomask 4a. The effective light source of the illumination optical system 13 and the surface of the semiconductor substrate 1 can be on the optical conjugate plane with each other by moving the surface of the semiconductor substrate 1 by a distance Ldf, for example, 30 μm in a direction opposite to the projection optical system 15 from the optical conjugate plane of the front surface of the inspection photomask 4a. Accordingly, images of the effective light source of the illumination optical system 13 are projected onto the semiconductor substrate 1. As a result, an inspection pattern is transferred onto the resist film of the semiconductor substrate 1, allowing detection of a local defect of the illumination optical system 13 in the exposure tool.

According to the inspection method of the second modification of the embodiment of the present invention, inspection processing for the local defect of the illumination optical system can be easily implemented within a short time.

(Third Modification)

Figure 19:
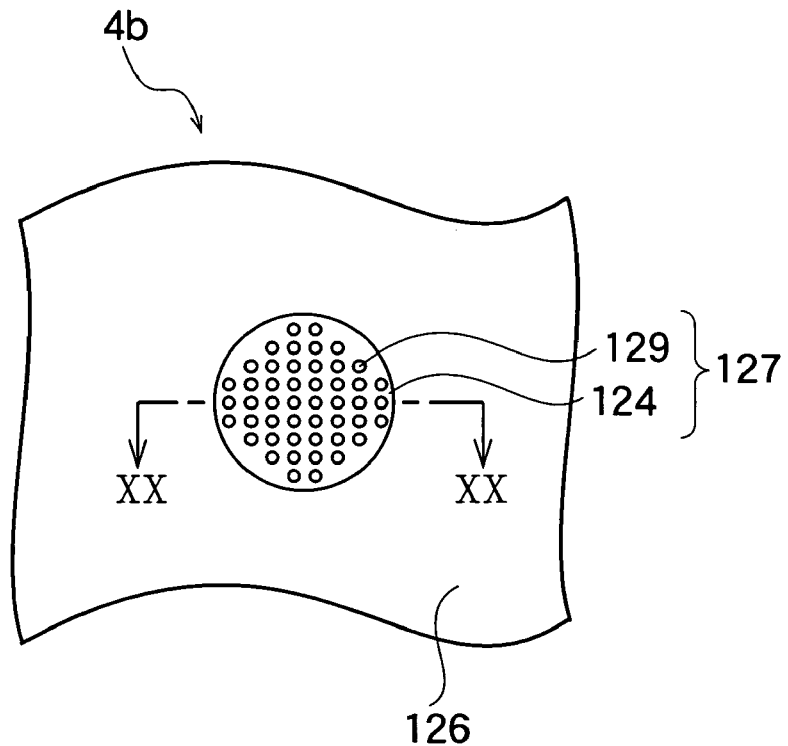
FIG. 19 is a view for describing an example of an inspection photomask for an inspection method according to a third modification of the embodiment of the present invention.
Figure 20:
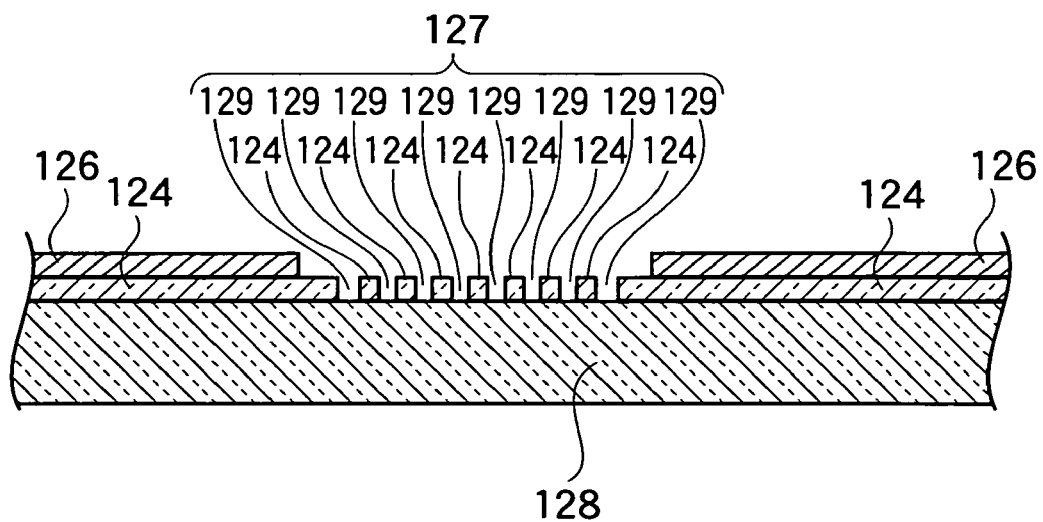
FIG. 20 is a cross-sectional view of the inspection photomask taken along line XX-XX in FIG. 19.

As shown in FIG. 19, in an inspection photomask 4b used for an inspection method according to a third modification of the embodiment of the present invention, an opaque film 126 has a pinhole 127 made from a translucent film 124 having a plurality of circular transparent portions 129 arranged in a grid pattern. Note that the single pinhole 127 of the inspection photomask 4b is shown in FIG. 19, however, the inspection photomask 4b includes a plurality of pinholes the same as pinhole 127, which are omitted in the drawing. As shown in FIG. 20, the pinhole 127 configures a diffraction grating with circular transparent portions 129, which are two-dimensionally and repeatedly arranged in the translucent film 124 disposed in between the transparent substrate 128 and the opaque film 126. The translucent film 124 has a transmittance of 6% and provides a phase difference of 180 degrees in the light passing through the translucent film 124 with the light passing through a transparent portion 129. Since the configuration of the third modification of the embodiment of the present invention is the same as that of the embodiment of the present invention except for the pinholes 127 of the inspection photomask 4b which configures the diffraction grating with the translucent film 124 and transparent portions 129, duplicate description is omitted.

Figure 21:
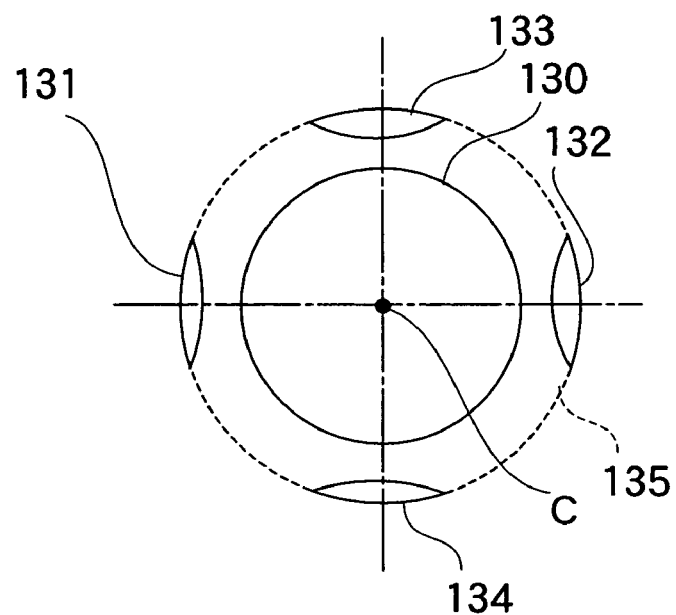
FIG. 21 is a diagram for describing an example of an inspection pattern generated onto the semiconductor substrate from the inspection photomask for the inspection method according to the third modification of the embodiment of the present invention.

When an exposure process is carried out with the exposure tool shown in FIG. 1 using the inspection photomask 4b according to the third modification of the embodiment of the present invention, exposure beams are diffracted by the diffraction grating of the pinhole 127, and a plurality of effective light source images are projected onto a resist film on the surface of the semiconductor substrate 1. For example, as shown in FIG. 21, an inspection pattern 130, which is transferred from a zeroth-order diffraction beam, and first through fourth first-order diffraction images 131 through 134, which are transferred from four first-order diffraction beams, are formed around the inspection pattern 130. The inspection pattern 130 is an effective light source image of the illumination optical system 13, which is transferred through the pinholes 127, as with the inspection pattern, which is transferred from the inspection photomask 4 according to the embodiment of the present invention. Therefore, inspection processing for a local defect of the illumination optical system 13 can be implemented using the inspection pattern 130. On the other hand, the first and the second first-order diffraction images 131 and 132, which face each other, and the third and the fourth first-order diffraction images 133 and 134, which face each other in a direction perpendicular to the line from the first first-order diffraction image 131 to the facing second first-order diffraction image 132, are the effective light source images from the first-order diffraction beams, which are partially shielded by a circular outer edge 135 corresponding to the circular aperture stop 16 in the projection optical system 15. Here, the outer edge 135 corresponds to the boundary of the aperture stop 16 and reflects the size of the aperture stop 16 in the projection optical system 15. Therefore, the radius of the outer edge 135 is in proportion to the numerical apertures (NA) on an output side of the projection optical system 15.

Figure 22:
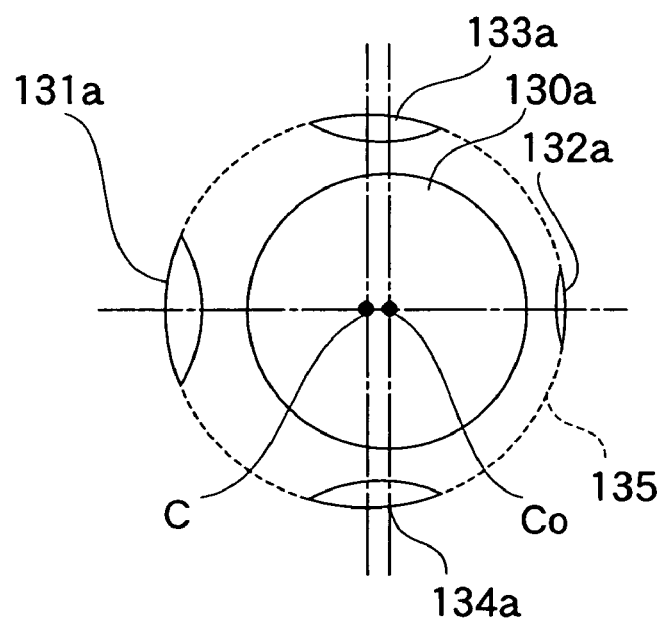
FIG. 22 is a diagram for describing another example of an inspection pattern generated onto the semiconductor substrate from the inspection photomask for the inspection method according to the third modification of the embodiment of the present invention.

If the illumination optical system 13 and the projection optical system 15 are normal, the center C of the outer edge 135 will match with the center of the inspection pattern 130, as shown in FIG. 21. For example, as shown in FIG. 22, the center C of the outer edge 135 deviates from the center Co of the inspection pattern 130a. A variation between the center C of the outer edge 135 and the center Co of the inspection pattern 130a is defined as an "illumination telecentricity error". The illumination telecentricity error is, for example, as described in the foregoing publication (Proceedings of SPIE, March, 1999, Vol. 3679, p. 87-98), caused by an aberration of the condenser lens 12, and may cause deterioration in imaging characteristics. In the example shown in FIG. 22, the illumination telecentricity error occurs where the center Co of the inspection pattern 130a deviates in a direction from the first first-order diffraction image 131a towards the second first-order diffraction image 132a, which faces the first first-order diffraction image 131a. Generally, the illumination telecentricity error depends on an aberration of the condenser lens 12 and occurs in an arbitrary direction on the surface in which the inspection pattern 130a and the first through fourth first-order diffraction images 131a through 134a are formed. By using the variation between the center Co of the inspection pattern 130a and the center C of the outer edge 135 provided from the peripheries of the first through the fourth first-order diffraction images 131a through 134a due to the first-order diffraction beams, as image data, inspection processing for the aberration of the condenser lens 12, which causes an illumination telecentricity error, can be implemented.

In addition, the numerical apertures NA on the output side of the projection optical system 15 may vary due to a production variance of the exposure tool. The numerical apertures NA on the output side of the projection optical system 15 relates to the resolution and the depth of focus of the exposure tool. Therefore, a variation of the numerical apertures NA on the output side of the projection optical system 15 may cause a variation in transferred resist pattern dimensions. The size of the numerical apertures NA on the output side of the projection optical system 15 corresponds to the outer edge 135. Therefore, usage of the diameter of the outer edge 135 as image data, which is provided by image processing, allows inspection of the variation in the numerical apertures NA on the output side of the projection optical system 15.

According to the inspection method of the third modification of the embodiment of the present invention, inspection processing for a local defect of the illumination optical system 13 can be easily implemented within a short time. In addition, according to the inspection method of the third modification of the embodiment of the present invention, inspection processing for the aberration of the condenser lens 12 in the illumination optical system 13 or for the variation in the numerical apertures NA on the output side of the projection optical system 15 can be easily performed within a short time.

Other Embodiments

According to the inspection method of the embodiment of the present invention, the inspection photomask 4 is placed facing upward so that the front surface of the inspection photomask 4 in which the pinholes 24a through 24h are arranged, faces the illumination optical system 13. Alternatively, the pinholes may be provided at certain positions other than on the front surface of the photomask. For example, pinholes may be provided on a pellicle, which is used to protect the surface of a photomask, made of an opaque material. Alternatively, pinholes may be provided either in a space between the mask stage 14 and the illumination optical system 13 or the projection optical system 15, or a space between the projection optical system 15 and the substrate stage 18. Even in such a case, since the plane of the pinholes deviates from the optical conjugate plane of the surface of the semiconductor substrate 1, needless to say, the same effect as with the embodiment of the present invention can be obtained.

Various modifications will become possible for those skilled in the art after storing the teachings of the present disclosure without departing from the scope thereof.

What is claimed is:

1. An inspection method for an illumination optical system of an exposure tool, comprising:
    coating a surface of an exposure target substrate with a resist film;
    placing a plurality of imaging components provided on a front surface of a photomask, the front surface deviating from an optical conjugate plane of a surface of the resist film;
    forming a plurality of inspection patterns of the resist film having a plurality of openings, by development after projecting exposure beams output from a plurality of effective light sources onto the resist film via the imaging components, each of the openings corresponding to each of the effective light sources, each of the inspection patterns corresponding to each of the imaging components, the effective light sources being placed on a different optical conjugate plane than the surface of the resist film;
    measuring one of the inspection patterns as a reference image, and processing the reference image so as to provide reference image data;
    measuring inspection images of the inspection patterns, and processing the inspection images with the reference image data so as to provide a plurality of inspection image data; and
    determining an abnormal inspection image by comparing the inspection image data with the reference image data.

2. The inspection method of claim 1, wherein the reference image data and the inspection image data include at least one of a brightness of the inspection image of the inspection pattern and a shape of the inspection pattern.

3. The inspection method of claim 1, wherein the abnormal inspection image occurs due to a defect including at least one of dust, a scratch in an illumination optical system which forms the effective light source, and an aberration of the illumination optical system.

4. The inspection method of claim 1, wherein the imaging components are a plurality of pinholes provided in an opaque film.

5. The inspection method of claim 1, wherein the imaging components are a plurality of lenses in a lens array.

6. The inspection method of claim 4, wherein the pinholes implement a diffraction grating having a translucent film and a transparent portion arranged in a grid pattern.

7. The inspection method of claim 6, wherein the reference image data and the inspection image data further include a variation of a center position between at least one of the inspection patterns formed by a zeroth-order diffraction beam of the diffraction grating and an outer edge formed by a plurality of first-order diffraction beams, and a size of the outer edge.

8. A processor for inspecting an illumination optical system of an exposure tool, comprising:
    a data input module configured to acquire a reference image and inspection images of a plurality of inspection patterns of a resist film having a plurality of openings, the inspection patterns formed by development after projecting exposure beams output from a plurality of effective light sources onto the resist film coated on a surface of an exposure target substrate by a plurality of imaging components provided on a front surface of a photomask, the imaging components placed so that the front surface deviates from an optical conjugate plane of the surface of the resist film, each of the openings corresponding to each of the effective light sources, each of the inspection patterns corresponding to each of the imaging components, the effective light sources being placed on a different optical conjugate plane than the surface of the resist film;

an image processing module configured to calculate reference image data and inspection image data from the reference image and the inspection images, respectively; and a determination module configured to compare the inspection image data with the reference image data, so as to determine whether the inspection image is an abnormal inspection image.

9. The processor of claim 8, wherein the reference image data and the inspection image data include at least one of a brightness of the inspection image of the inspection pattern and a shape of the inspection pattern.

10. The processor of claim 8, wherein the abnormal inspection image occurs due to a defect including at least one of dust, a scratch in an illumination optical system which forms the effective light source, and an aberration of the illumination optical system.

11. The processor of claim 8, wherein the imaging components are a plurality of pinholes provided in an opaque film.

12. The processor of claim 8, wherein the imaging components are a plurality of lenses in a lens array.

13. The processor of claim 11, wherein the pinholes implement a diffraction grating having a translucent film and a transparent portion arranged in a grid pattern.

14. The processor of claim 13, wherein the reference image data and the inspection image data further include a variation of a center position between at least one of the inspection patterns formed by a zeroth-order diffraction beam of the diffraction grating and an outer edge formed by a plurality of first-order diffraction beams, and a size of the outer edge.

15. A method for manufacturing a semiconductor device, comprising:

executing an inspection processing of an exposure tool including:

coating a surface of an inspection target substrate with an inspection resist film;

placing a plurality of imaging components provided on a front surface of an inspection photomask, the front surface deviating from an optical conjugate plane of a surface of the inspection resist film;

forming a plurality of inspection patterns of the inspection resist film having a plurality of openings, by development after projecting exposure beams output from a plurality of effective light sources onto the inspection resist film via the imaging components, each of the openings corresponding to each of the effective light sources, each of the inspection patterns corresponding to each of the imaging components, the effective light sources being placed on a different optical conjugate plane than the surface of the resist film;

measuring one of the inspection patterns as a reference image, and processing the reference image so as to provide reference image data; and determining an abnormal inspection image by measuring inspection images of the inspection patterns and comparing a plurality of inspection image data provided by processing the inspection images with the reference image data;

correcting the exposure tool by acquiring a type of defect from the abnormal inspection image when the abnormal inspection image is determined to occur;

coating a semiconductor substrate with a manufacturing resist film;

loading a manufacturing photomask and the semiconductor substrate to the exposure tool, and subjecting the semiconductor substrate to a manufacturing process of a semiconductor device by delineating the manufacturing resist film using the manufacturing photomask.

16. The method of claim 15, wherein the reference image data and the inspection image data include at least one of a brightness of the inspection image of the inspection pattern and a shape of the inspection pattern.

17. The method of claim 15, wherein the abnormal inspection image occurs due to a defect including at least one of dust, a scratch in an illumination optical system which forms the effective light source, and an aberration of the illumination optical system.

18. The method of claim 15, wherein the imaging components are a plurality of pinholes provided in an opaque film.

19. The method of claim 15, wherein the imaging components are a plurality of lenses in a lens array.

20. The method of claim 18, wherein the pinholes implement a diffraction grating having a translucent film and a transparent portion arranged in a grid pattern.

* * * * *